(12) United States Patent
Strich et al.

(10) Patent No.: US 10,322,164 B2
(45) Date of Patent: Jun. 18, 2019

(54) MODULATION OF CELLULAR LOCALIZATION OF CYCLIN C

(71) Applicant: Rowan University, Glassboro, NJ (US)

(72) Inventors: Randy Strich, Medford Lakes, NJ (US); Katrina Cooper, Medford Lakes, NJ (US)

(73) Assignee: Rowan University, Glassboro, NJ (US)

( * ) Notice: Subject to any disclaimer, the term of this patent is extended or adjusted under 35 U.S.C. 154(b) by 0 days.

(21) Appl. No.: 15/112,360

(22) PCT Filed: Jan. 16, 2015

(86) PCT No.: PCT/US2015/011862
§ 371 (c)(1),
(2) Date: Jul. 18, 2016

(87) PCT Pub. No.: WO2015/109258
PCT Pub. Date: Jul. 23, 2015

(65) Prior Publication Data
US 2016/0367630 A1    Dec. 22, 2016

Related U.S. Application Data

(60) Provisional application No. 61/928,203, filed on Jan. 16, 2014.

(51) Int. Cl.
| | |
|---|---|
| *A61K 38/17* | (2006.01) |
| *A61K 45/06* | (2006.01) |
| *C07K 14/47* | (2006.01) |
| *C12N 7/00* | (2006.01) |
| *G01N 33/50* | (2006.01) |

(52) U.S. Cl.
CPC .......... *A61K 38/1709* (2013.01); *A61K 45/06* (2013.01); *C07K 14/4738* (2013.01); *C12N 7/00* (2013.01); *G01N 33/5011* (2013.01); *C07K 2319/03* (2013.01); *C12N 2740/16311* (2013.01); *C12N 2740/16322* (2013.01)

(58) Field of Classification Search
None
See application file for complete search history.

(56) References Cited

U.S. PATENT DOCUMENTS

| 6,075,123 | A | 6/2000 | Lahti et al. | |
|---|---|---|---|---|
| 7,786,072 | B2 | 8/2010 | Verdine et al. | |
| 2002/0142983 | A1* | 10/2002 | Agrawal | C07K 14/4727 514/44 A |
| 2003/0105000 | A1* | 6/2003 | Pero | A61K 38/06 514/19.3 |
| 2012/0195978 | A1 | 8/2012 | Hickey et al. | |
| 2013/0005650 | A1 | 1/2013 | Chiang | |

FOREIGN PATENT DOCUMENTS

| WO | 9841648 A2 | 9/1998 | |
|---|---|---|---|
| WO | 0109373 A2 | 2/2001 | |
| WO | WO-2008151200 A2 * | 12/2008 | ............. C07K 14/47 |
| WO | 2013040142 A2 | 3/2013 | |

OTHER PUBLICATIONS

Rapoport & Lorberoum-Galski (Expert Opinion on Drug Delivery 2009 6 (5): 453-463) (Year: 2009).*
Ohata et al. (Int. J. Mol. Med. 2006 18: 1153-1158) (Year: 2006).*
Ibragimova and Wade (Biophysical Journal, Oct. 1999, vol. 77, pp. 2191-2198) (Year: 1999).*
Rudikoff et al. (PNAS USA, 1982, 79: 1979-1983) (Year: 1982).*
Burgess et al. (J of Cell Bio. 111:2129-2138, 1990) (Year: 1990).*
Hoeppner et al. J. Mol. Biol. 2005 350: 833-842 (Year: 2005).*
Cooper and Strich (Gene Expression 1999 8: 43-57). (Year: 1999).*
Verdine and Hilinski (Methods in Enzymology 2012 503: 3-33) (Year: 2012).*
Cisplatin (National Cancer Institute Jul. 16, 2012, https://web.archive.org/web/20121216233142/http://cancer.gov/cancertopics/druginfo/cisplatin/print) (Year: 2012).*
Tannock, I.F. (Experimental Chemotherapy, Ch. 19—p. 338 and 352-359, in The Basic Science of Oncology Tannock and Hill, eds., New York 1992) (Year: 1992).*
Jin et al., "The Cell Wall Sensors Mtl1, Wsc1, and Mid2 Are Required for Stress-Induced Nuclear to Cytoplasmic Translocation of Cyclin C and Programmed Cell Death in Yeast," Oxidative Medicine and Cellular Longevity (2013); 2013:1-15.
Cooper et al., "Stress-Induced Nuclear to Cytoplasmic Translocation of Cyclin C Promotes Mitochondrial Fission in Yeast," Dev. Cell (Jan. 27, 2014); 28(2):161-173.
Adachi, et al., "Cyclin C: an Inducer of Mitochondrial Division Hidden in the Nucleus," Developmental Cell, Cell Press, US, vol. 28, No. 2, Jan. 2014, pp. 112-114.
Casimiro, et al., "Cyclins and Cell Cycle Control in Cancer and Disease," Genes and Cancer, vol. 3, No. 11-12, 2012, pp. 649-657.
Jin, et al., "Slt2p Phosphorylation Induces Cyclin C Nuclear-to-Cytoplasmic Translocation in Response to Oxidative Stress," Molecular Biology of the Cell, vol. 25, No. 8, 2014, pp. 1396-1407.
Leopold, et al., "An Evolutionarily Conserved Cyclin Homolog from *Drosophila* Rescues Yeast Deficient in G1 Cyclins," Cell, vol. 66, No. 6, 1991, pp. 1207-1216. Abstract Only.
Li, et al., "Molecular Cloning and Chromosomal Localization of the Human Cyclin C (CCNC) and Cyclin E (CCNE) Genes: Deletion of the CCNC Gene in Human Tumors," Genomics, Academic Press, San Diego, US, vol. 32, No. 2, 1996, pp. 253-259. Abstract Only.
Rickert, et al., "Cyclin C/CDK8 is a Novel CTD Kinase Associated with RNA Polymerase II," Oncogene, vol. 12, No. 12, 1996, pp. 2631-2640.

(Continued)

*Primary Examiner* — Peter J Reddig
(74) *Attorney, Agent, or Firm* — Saul Ewing Arnstein & Lehr LLP; Domingos J. Silva

(57) ABSTRACT

Provided are methods and compositions for treatment of cancer. In particular, these methods and compositions may include a compound that induces the translocation of cyclin C from the cell nucleus to the cytoplasm. Also provided are methods of screening tumor cells for susceptibility to compounds that induce the translocation of cyclin C.

16 Claims, 19 Drawing Sheets

Specification includes a Sequence Listing.

(56) References Cited

OTHER PUBLICATIONS

Strich, et al., "The Dual Role of Cyclin C Connects Stress Regulated Gene Expression to Mitochondrial Dynamics," Microbial Cell, vol. 1, No. 10, 2014, pp. 318-324.
Wang, et al., "Cyclin C Mediates Stress-Induced Mitochondrial Fission and Apoptosis," Molecular Biology of the Cell, vol. 26, No. 6, 2015, pp. 1030-1043.

\* cited by examiner

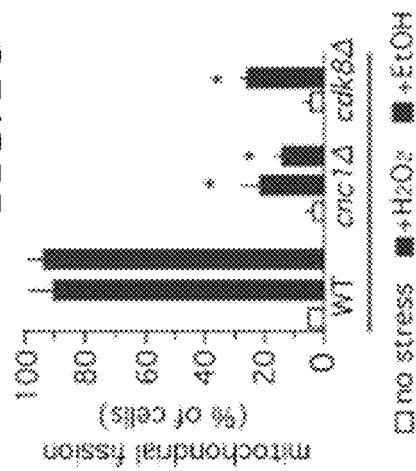
FIG. 2A
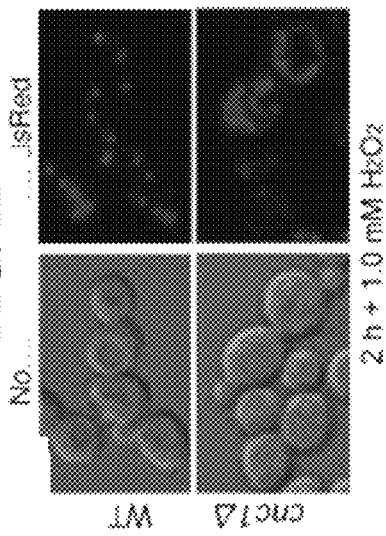
FIG. 2B
FIG. 2C
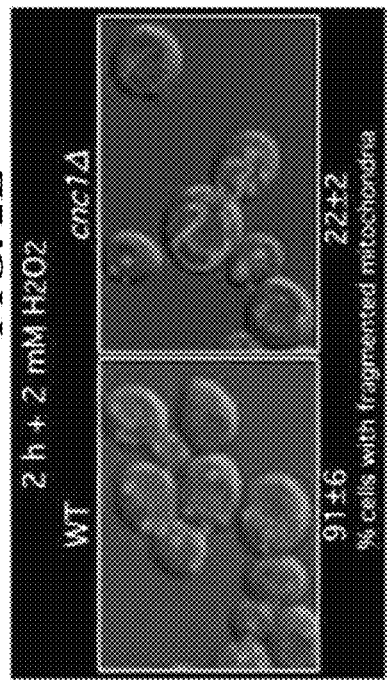
FIG. 2D
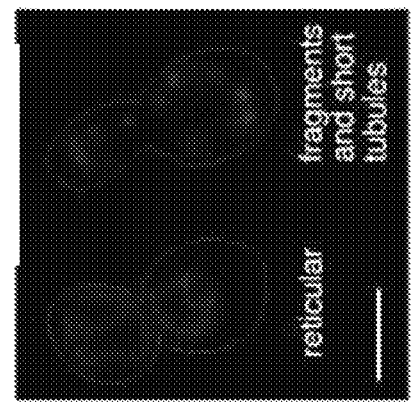
FIG. 2E
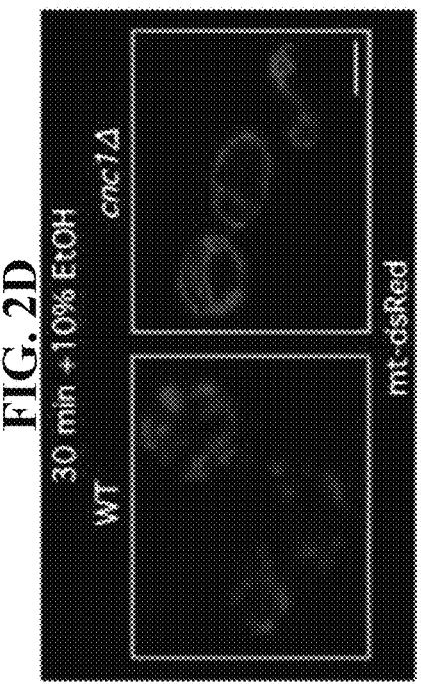

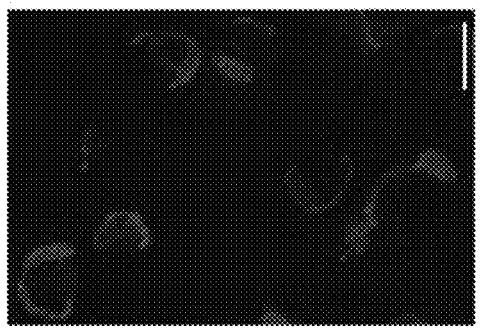
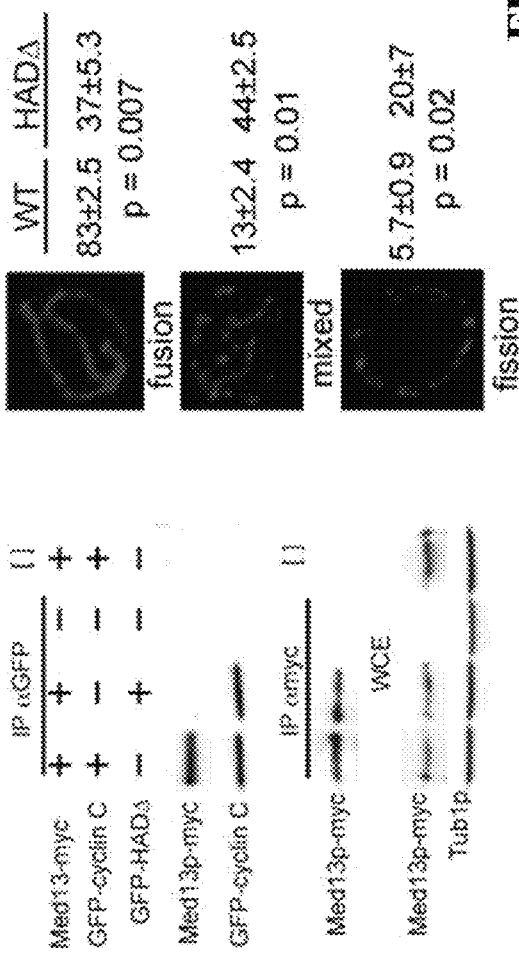
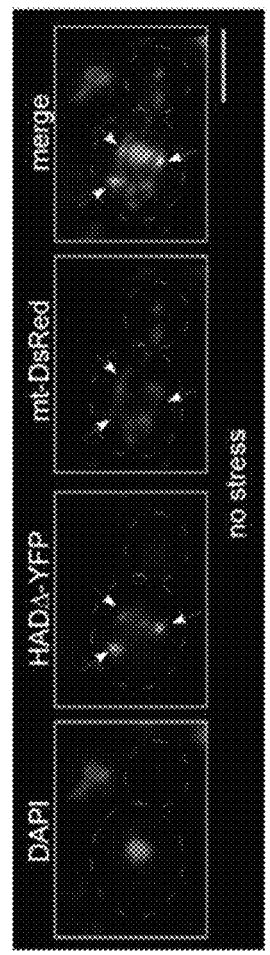

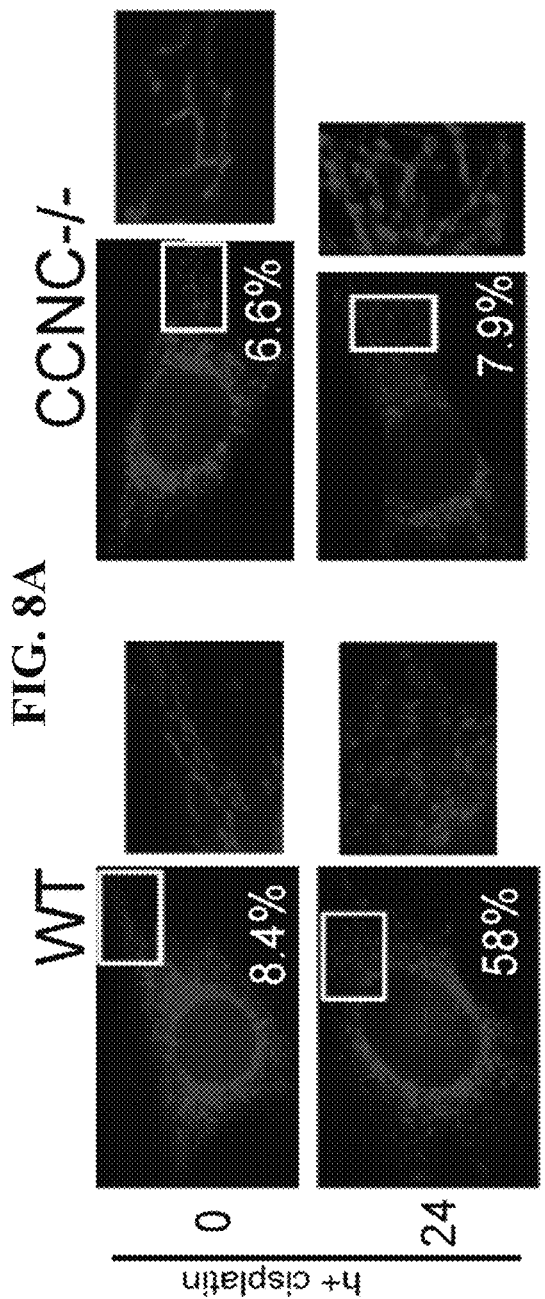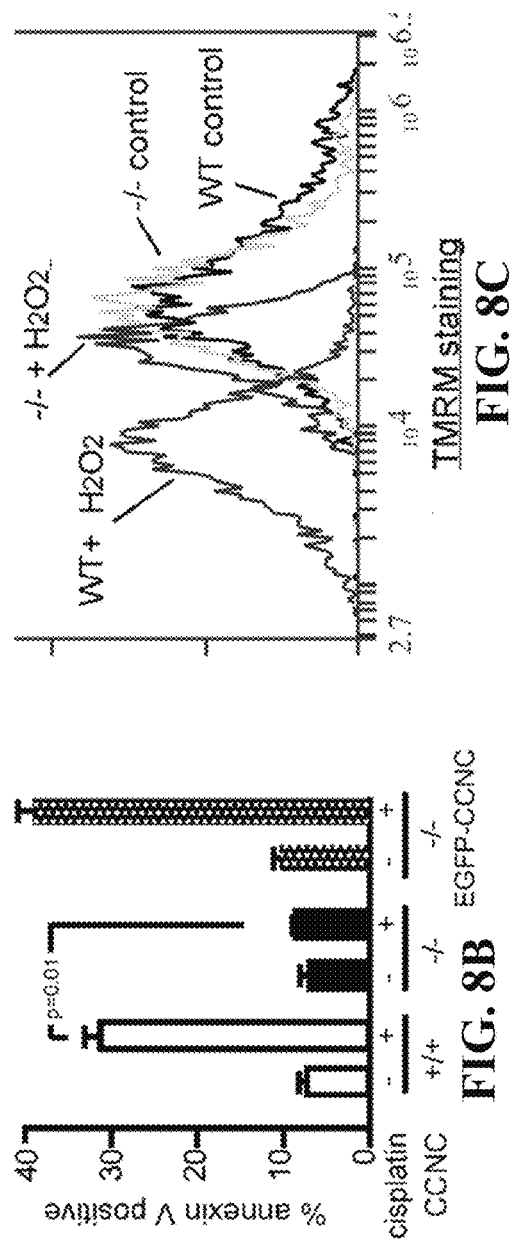

human MAGNFWQSSHLYQWILDKQDLIKERQKDIKFL (SEQ ID NO: 9)
rat   MAGNFWQSSHLYQWILD       KERQKDIKFL (SEQ ID NO: 10)
fly   MAGNFWQSSHSQQWILDKPDLIRERQHDLLAL (SEQ ID NO: 11)
yeast MSGSFWTSTQRHHWQYTKASLAKERQKLWLLE (SEQ ID NO: 12)

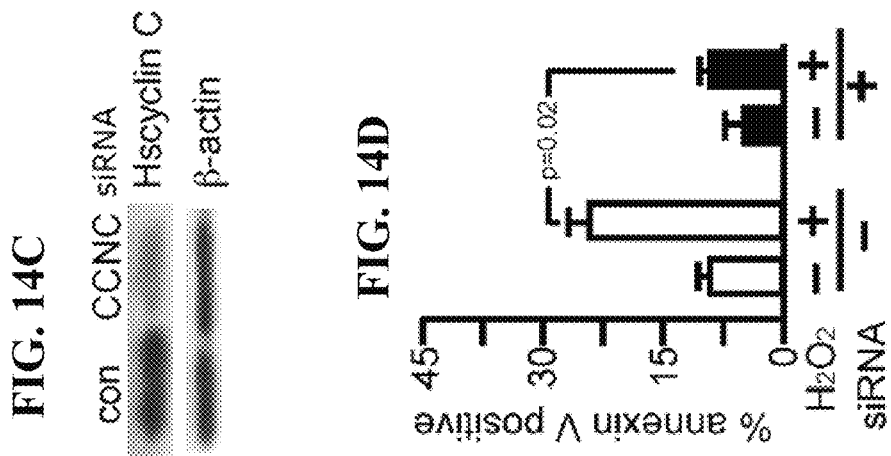
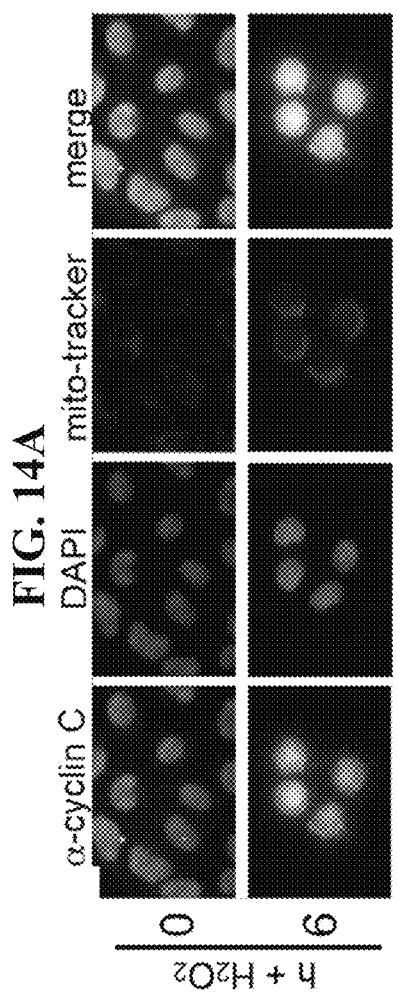
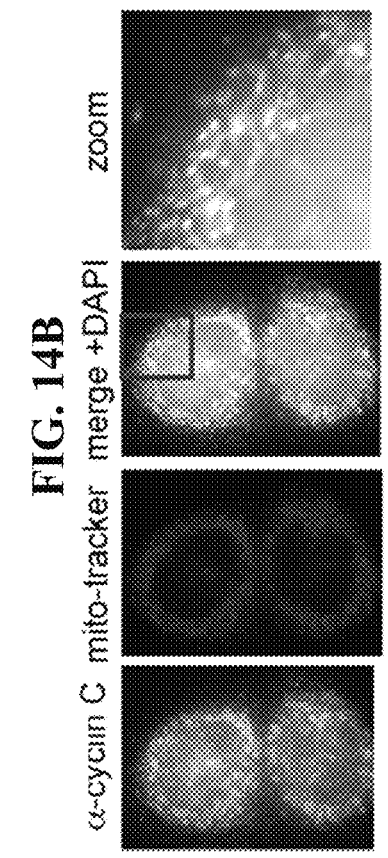

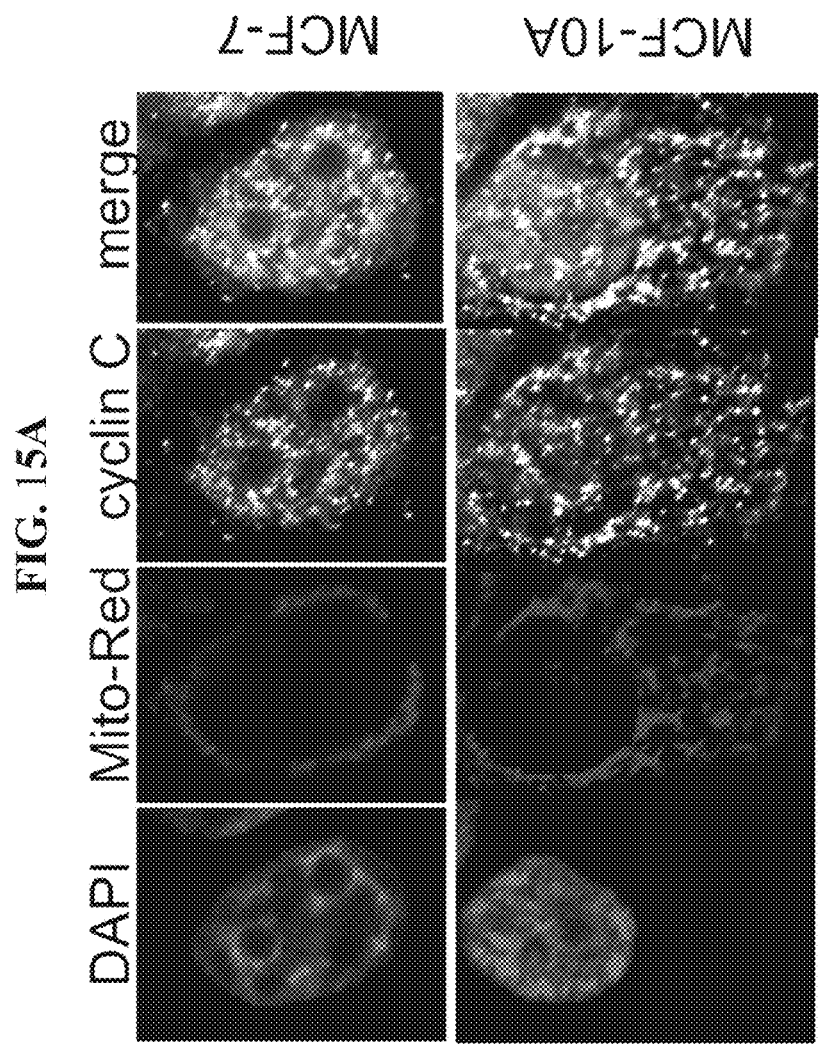

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial
<220> FEATURE:
<223> OTHER INFORMATION: Synthetic

<400> SEQUENCE: 1

Tyr Gly Arg Lys Lys Arg Arg Gln Arg Arg Arg
1               5                   10

<210> SEQ ID NO 2
<211> LENGTH: 16
<212> TYPE: PRT
<213> ORGANISM: Artificial
<220> FEATURE:
<223> OTHER INFORMATION: Synthetic

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic

<400> SEQUENCE: 3

Arg Arg Arg Arg Asn Arg Thr Arg Arg Asn Arg Arg Arg Val Arg
1               5                   10                  15

<210> SEQ ID NO 4
<211> LENGTH: 7
<212> TYPE: PRT
<213> ORGANISM: Artificial
<220> FEATURE:
<223> OTHER INFORMATION: Synthetic

<400> SEQUENCE: 4

Lys Glu Arg Gln Lys Asp Leu
1               5

<210> SEQ ID NO 5
<211> LENGTH: 16
<212> TYPE: PRT
<213> ORGANISM: Artificial
<220> FEATURE:
<223> OTHER INFORMATION: Synthetic
```

<400> SEQUENCE: 5

Trp Ile Leu Asp Lys Gln Asp Leu Leu Lys Glu Arg Gln Lys Asp Leu
1               5                   10                  15

<210> SEQ ID NO 6
<211> LENGTH: 30
<212> TYPE: PRT
<213> ORGANISM: Artificial
<220> FEATURE:
<223> OTHER INFORMATION: Synthetic

<400> SEQUENCE: 6

Tyr Gly Arg Lys Lys Arg Arg Gln Arg Arg Trp Ile Leu Asp Lys
1               5                   10                  15

Gln Asp Leu Leu Lys Glu Arg Gln Lys Asp Leu Lys Phe Leu
            20                  25                  30

<210> SEQ ID NO 7
<211> LENGTH: 18
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 7

Met Ala Gly Asn Phe Xaa Gln Ser Ser His Tyr Leu Gln Trp Ile Leu
1               5                   10                  15

Asp Lys

<210> SEQ ID NO 8
<211> LENGTH: 18
<212> TYPE: PRT
<213> ORGANISM: Homo sapiens

<400> SEQUENCE: 8

Ile Leu Asp Lys Gln Asp Leu Leu Lys Glu Arg Gln Lys Asp Leu Lys
1               5                   10                  15

Phe Leu

<210> SEQ ID NO 9
<211> LENGTH: 32
<212> TYPE: PRT
<213> ORGANISM: Homo sapiens

<400> SEQUENCE: 9

Met Ala Gly Asn Phe Trp Gln Ser Ser His Tyr Leu Gln Trp Ile Leu
1               5                   10                  15

Asp Lys Gln Asp Leu Leu Lys Glu Arg Gln Lys Asp Leu Lys Phe Leu
            20                  25                  30

<210> SEQ ID NO 10
<211> LENGTH: 27
<212> TYPE: PRT
<213> ORGANISM: Rattus rattus

<400> SEQUENCE: 10

Met Ala Gly Asn Phe Trp Gln Ser Ser His Tyr Leu Gln Trp Ile Leu
1               5                   10                  15

Asp Lys Glu Arg Gln Lys Asp Leu Lys Phe Leu
            20                  25

```
<210> SEQ ID NO 11
<211> LENGTH: 32
<212> TYPE: PRT
<213> ORGANISM: Drosophila melanogaster

<400> SEQUENCE: 11

Met Ala Gly Asn Phe Trp Gln Ser Ser His Ser Gln Gln Trp Ile Leu
1               5                   10                  15

Asp Lys Pro Asp Leu Leu Lys Glu Arg Gln Lys Asp Leu Leu Ala Leu
            20                  25                  30

<210> SEQ ID NO 12
<211> LENGTH: 32
<212> TYPE: PRT
<213> ORGANISM: Saccharomyces cerevisiae

<400> SEQUENCE: 12

Met Ser Gly Ser Phe Trp Thr Ser Thr Gln Arg His His Trp Gln Tyr
1               5                   10                  15

Thr Lys Ala Ser Leu Ala Lys Glu Arg Gln Lys Leu Trp Leu Leu Glu
            20                  25                  30
```

MODULATION OF CELLULAR LOCALIZATION OF CYCLIN C

CROSS-REFERENCE TO RELATED APPLICATIONS

The present application is a U.S. National Phase of International Patent Application No. PCT/US2015/011862, filed Jan. 16, 2015, which claims the benefit of U.S. Provisional Application No. 61/928,203 filed on Jan. 16, 2014, the disclosures of which are hereby incorporated by reference in their entirety.

STATEMENT REGARDING FEDERALLY SPONSORED RESEARCH

This invention was made, at least in part, with government support under grant numbers RO1CA099003 and RO1GM086788 awarded by the National Institutes of Health (NIH). The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 16, 2015, is named 125107_00023_ST25 and is 4.0 kilobytes in size.

TECHNICAL FIELD OF THE INVENTION

In certain aspects, the present invention relates to compounds and methods useful in inducing translocation of cyclin C and sensitizing tumor cells to anti-cancer drugs and reactive oxygen species (ROS) from internal or external sources.

BACKGROUND OF THE INVENTION

Current therapeutic interventions for treating cancerous conditions focus on inhibiting cancer cell propagation by killing, extracting or retarding their growth. The role of mitochondria in promoting cell death has drawn much attention as a potential target for the next generation of anti-cancer agents. Mitochondria are a key regulatory node for the stress-activated intrinsic programmed cell death (PCD). Mitochondria are dynamic organelles undergoing constant fusion and fission during normal cell division. The equilibrium between fission and fusion is controlled by the activity of conserved molecular machines driven by dynamin-like GTPases (Westermann, 2010). In response to cytotoxic damage, the mitochondria may undergo extensive fission accompanied by mitochondrial outer membrane permeability (MOMP) which releases sequestered pro-apoptotic proteins into the cytoplasm. In budding yeast, mitochondrial fission requires the GTPase Dnm1p that forms atypical helical filaments that first encircle, then constrict, mitochondria until scission is achieved (Mears et al., 2011). Recruitment of Dnm1p to the mitochondria requires the outer membrane protein Fis1p (Mozdy et al., 2000; Tieu et al., 2002) and one of two adaptor proteins, Mdv1p (Mozdy et al., 2000; Tieu and Nunnari, 2000) or Caf4p (Griffin et al., 2005). On the other side of the equation, the fusion of the inner and outer mitochondrial membranes requires the Mgm1p and Fzo1p GTPases, respectively (Meeusen et al., 2006; Rapaport et al., 1998). Several studies have demonstrated that the proper balance of fission and fusion is required for normal mitochondrial function (Ishihara et al., 2009; Wakabayashi et al., 2009).

The balance between fission and fusion is shifted dramatically toward fission in cells exposed to exogenous stress (Westermann, 2010). Mitochondrial hyper-fission is a conserved hallmark of the stress response (Igaki et al., 2000; Karbowski et al., 2002; Vieira et al., 2002) and is associated with the release of sequestered programmed cell death (PCD) inducing factors from this organelle (Breckenridge et al., 2003; Frank et al., 2001).

At least one underlying mechanism allowing tumor progression and resistance to anti-cancer therapies is the ability of cancerous cells to inhibit the intrinsic PCD pathway. For example, overexpression of the B Cell lymphocyte 2 (Bcl-2) pro-survival BH3 protein prevents MOMP. Such overexpression is observed in a high percentage of chronic lymphocytic leukemia (CLL) patients. However, efforts to design therapies that inactivate pro-survival proteins or stimulate pro-death components have been hampered due to a fundamental lack of understanding about how other pathways impinge on mitochondrial function and PCD induction. As such there is a need in the art to further identify the correlation among various components that activate or deactivate the cell death system in patients suffering from cancer and thereby improve or supplement available methods of treatment in the fight against cancer. Such knowledge can further lead to discovery of new therapeutic compositions and methods of applying or administering the same to treat hyperplasia or cancerous conditions in subjects in need of such treatment.

BRIEF SUMMARY OF THE INVENTION

In one aspect, the present invention provides a method of inhibiting tumor growth or sensitizing a tumor cell to a therapeutic agent comprising contacting a tumor cell with a compound capable of inducing the nuclear to cytoplasmic translocation of cyclin C.

In another aspect, the present invention provides a compound capable of inducing the nuclear to cytoplasmic translocation of cyclin C.

In another aspect, the present invention provides a compound comprising the holoenzyme association domain (HAD) of cyclin C or a fragment or mimetic thereof.

In another aspect, the present invention provides a method of identifying a combination of a tumor cell type and an anti-tumor agent whose action is susceptible to enhancement by cyclin C translocation.

BRIEF DESCRIPTION OF THE DRAWINGS

(FIG. 1A) Fluorescence microscopy was conducted on mid-log phase cells expressing cyclin C-YFP and the DsRed mitochondrial targeting plasmid (mt-DsRed) before (0 h) and following (2 h) 1 mM $H_2O_2$ treatment. Arrows indicate sites of cyclin C-YFP and mitochondrial co-localization. (FIG. 1B) As in (FIG. 1A) except that living cells were visualized omitting DAPI staining. (FIG. 1C) Western blot analysis of cyclin C-TAP in whole cell extracts (WCE) or mitochondrial enriched fractions prepared from cultures with the indicated genotypes before and after $H_2O_2$ exposure (0.8 mM). The blot was stripped and reprobed for the presence of Npl3p (nuclear) and Pori p (mitochondria)) markers. (FIG. 1D) Western blot analysis of cyclin C-TAP in the 1 hr VVT mitochondrial fraction described in (FIG. 1C)

with (+) and without (−) Proteinase K treatment. Molecular weight markers (kDa) are indicated on the left of the panel. This blot was stripped and probed for components of the outer (Porlp) and inner (Mam33p) mitochondrial membranes. (FIG. 1E) WT cells expressing cyclin C-YFP, Dnm1-cherry and mt-CFP expression plasmids were grown to mid-log phase then treated with 1 mM $H_2O_2$ as indicated. Co-localization (arrows) of the mitochondria, Cyclin C-YFP and Dnm1p-cherry was visualized by fluorescence microscopy. In all figures, the bars=5 μm unless otherwise stated. The enlarged regions are indicated by the grey boxes in all panels.

FIGS. 2A-2G provide that Cdk8p and cyclin C are required for stress-induced mitochondrial fission. (FIG. 2A) Representative images of reticular or fragmented mitochondria are shown. (FIG. 2B) Representative images of wild type and cnc1Δ Nomarski (Nom.) or mt-DsRed are shown following exposure to $H_2O_2$. (FIG. 2C) The percent of cells (mean±s.e.m.) within the population displaying mitochondrial fission is given before and following $H_2O_2$ (1 mM) or ethanol (10% vol/vol) treatment for 2 h or 30 min, respectively. * p<0.05. (FIG. 2D) Confocal microscopic images of WT and cnc1Δ strains expressing mt-DsRed following exposure to ethanol (10% vol/vol) for 30 min. (FIG. 2E) Combined Nomarski and fluorescence images were obtained from WT and cnc1Δ cultures expressing mt-DsRed before and following exposure to $H_2O_2$ (2 mM) for 2 h. The percent of the population exhibiting fragmented mitochondria was calculated from three independent cultures (average±s.e.m indicated). (FIG. 2F) A cdk8Δ strain (RSY1726) transformed with cyclin C-YFP and RFP-Nop1p expressing plasmids were visualized by fluorescence microscopy before and 2 h following $H_2O_2$ exposure (1 mM). DAPI staining indicates nuclear location. The arrows indicate the cyclin C-YFP foci observed in the stressed cdk8Δ cells. The frequency of cells containing a single focus associated with the nucleus is given on the right (mean±s.e.m. n=3). The remainder of the culture exhibited either a diffuse nuclear signal or contained ≥2 nuclear associated foci. (FIG. 2G) The percentage of cells displaying fission (mean±s.e.m.) in a cnc1Δ strain transformed with either the vector, wild type CNC1 or $CNC^{A110V}$ 2 h following $H_2O_2$ treatment (1 mM). *=p<0.01 compared to the CNC1 expressing plasmid FIGS. 3A-3E show that Cytoplasmic cyclin C is sufficient to induce fission. (FIG. 3A) Extracts prepared from a wild-type strain expressing endogenously tagged MED13-myc allele, GFP-cyclin C or the HADΔ derivative as indicated were immunoprecipitated with GFP antibodies and the resulting immunoprecipitates probed for the presence of Med13-13myc. This blot was stripped and reprobed for GFP to ensure similar expression levels between the two GFP-cyclin C proteins. Extracts immunoprecipitated with myc or whole cell extracts (WCE) directly probed for myc controlled for the presence of Med13-13myc in the extracts. indicates no antibody control lanes. (FIG. 3B) Fluorescence microscopy monitoring the location of cyclin $C^{HADΔ}$, the nucleus (DAPI) and mitochondria (mt-DsRed). Arrows indicate sites of mitochondria-cyclin $C^{HADΔ}$ interaction. Bar=5 μm. (FIG. 3C) A cnc1Δ mutant expressing either wild type or cyclin $C^{HADΔ}$ and mt-DsRed were grown to mid-log phase then examined by fluorescence microscopy. The cells were scored based on the mitochondria exhibiting a fusion, fission or mixed morphology (see Materials and methods for scoring metric). The mean values obtained from three independent transformants are presented (±s.e.m.) along with the p value. (FIG. 3D) The experiment in (FIG. 3C) was repeated with a dnm1Δ cnc1Δ mutant strain. (FIG. 3E) A wild-type strain (RSY10) harboring either myc-cyclin C or myc-cyclin $C^{HADΔ}$ expression plasmids was subjected to an oxidative stress timecourse. Extracts prepared from these samples were probed for cyclin C and cyclin $C^{HADΔ}$ levels by Western blot analysis. Tub1p levels were used as a loading control.

(FIG. 4A) Log phase fis1Δ cells harboring cyclin C-YFP and the mt-DsRed expression plasmids were treated with 1 mM $H_2O_2$ as indicated then examined by fluorescence microscopy. Arrows indicate cyclin C-YFP signals that do not associate with the mitochondria. Quantitation of the number of cyclin C-YFP foci associated with the mitochondria is given on the right (mean±s.e.m. n=3). Asterisks indicate p<0.01 from wild type value. (FIG. 4B) A dnm1Δ strain harboring cyclin C-YFP and mt-DsRed constructs was grown and analyzed as described in (FIG. 4A). White and gray arrows indicate cyclin C-YFP foci either not associating or associating with the mitochondria, respectively. (FIG. 4C) The experiment described in (FIG. 4B) was repeated with an mdv1Δ mutant. (FIG. 4D) Wild type, cnc1Δ, fis1Δ and cnc1Δfis1Δ mid-log phase cultures were treated with 1 or 2 mM $H_2O_2$ for 2 h then serially diluted (1:10) and plated onto rich growth medium. Plates were incubated three days prior to image collection.

(FIG. 6A) A wild-type strain transformed with Mdv1-GFP and mt-DsRed expressing plasmids were analyzed by confocal microscopy before and following $H_2O_2$ treatment (1 mM for 2 h). White arrows indicate sites of active fission, white arrows identify Mdv1p foci not associated with the mitochondria. (FIG. 6B) Mdv1p subcellular localization patterns in WT and cnc1Δ strains before and following $H_2O_2$ stress (1 mM for 2 h) were determined by confocal microscopy. The categories for Mdv1-GFP localization patterns are provided on the left. Values are mean±s.e.m. **=p<0.01. (FIG. 6C) Wild-type strain expressing cyclin C-YFP, Mdv1p-DsRed and mt-CFP was subjected to $H_2O_2$ stress (1 mM for 2 h). Subcellular localization of the proteins and mitochondria was monitored by fluorescence microscopy. The percentage of cyclin C-YFP foci associating with Mdv1p-DsRed is indicated (n=3). Arrows indicate regions of co-localization between cyclin C-YFP and Mdv1p in the enlarged images. (FIG. 6D) and (FIG. 6E) A two-hybrid reporter strain (gal1-HIS3, PJ69-4A) transformed with Gal4p DNA binding domain (DBD) and activator fusion protein combinations as indicated was patched onto medium selecting for reporter gene activation (−His). The previously reported Mdv1-DBD and Fis1-AD interaction (Griffin et al., 2005) was used as a positive control. Vec=vector control. (FIG. 6F) Extracts prepared from unstressed and stressed wild-type strain expressing endogenous cyclin C-TAP and Mdv1p-HA were incubated with αTAP or αHA antibodies then probed for the presence of cyclin C-TAP (top panel). Control immunoprecipitation of Mdv1p-HA is shown in the bottom panel. The control extracts not expressing endogenous Mdv1p-HA (−) are indicated.

(FIG. 7A) WT and cnc1Δ strains expressing MET25-Mdv1p-HA and MET25-Mdv1-myc were grown under non-inducing conditions for the MET25 promoter. Extracts prepared from samples taken before and following $H_2O_2$ addition were immunoprecipitated with αmyc then the immunoprecipitates probed for the presence of Mdv1p-HA. (FIG. 7B) Extracts prepared from stressed and unstressed wild type and cnc1Δ strains expressing Mdv1p-GFP and Dnm1p-myc were subjected to co-immunoprecipitation experiments as indicated (top panel). Bottom two panels control for Dnm1p-myc and Mdv1p-GFP expression levels in these extracts. [ ] indicate no antibody controls. (FIG. 7C) Co-localization of Mdv1p-GFP and Dnm1-cherry was examined in wild type and cnc1Δ strains before and following $H_2O_2$ treatment (1 mM) as indicated. Bar=5 μm. (FIG. 7D) A two-step model for cyclin C regulation of mitochondrial morphology and PCD. In unstressed cells, cyclin C (CC) and Cdk8 repress stress responsive genes. The mitochondria exhibit fused morphology in the majority of cells with Dnm1p and Mdv1p being located both in the cytoplasm and at the mitochondria. Step 1. Stress-induced translocated cyclin C associates with Mdv1p promoting Mdv1p-Dnm1p complex formation and extensive mitochondrial fragmentation. Step 2. Cyclin C disassociates from the fission complex and is destroyed by ubiquitin-mediated degradation. An additional stress signal, in combination with hyper-fission, is needed to complete the PCD pathway.

FIGS. 8A-8C demonstrate that cyclin C is required for mitochondrial fission and PCD. (FIG. 8A) Mitochondrial morphology in WT and CNCC$^{-/-}$MEFs before and after cisplatin treatment. % cells exhibiting hyper-fission is indicated. (FIG. 8B) PCD execution was determined in the cell lines indicated including a null MEF line expressing EGFP-cyclin C. (FIG. 8C) MOMP was monitored using the mitochondrial stain TMRM staining before (control) and following $H_2O_2$ treatment as indicated. Reduction TMRM staining indicates MOMP has occurred.

(FIG. 9A) Mice harboring floxed alleles of PTEN and CCNC expressing a thyroid-specific cre recombinase. Representative thyroids dissected from 20 wk old mice with the indicated genotypes. Thyroid/trachea weights are shown on the left. (FIG. 9B) Kaplan-Meyer survival plot for mice with the indicated genotype. n=6/genotype.

(FIG. 10A) Step 1: cyclin C disassociates from Med13 in response to stress. Step 2: cyclin C associates with Drp1 to induce mitochondrial fission which sensitizes the cell to anti-cancer drugs. (FIG. 10B) Deleting MED13 in yeast results in cyclin C cytoplasmic localization and mitochondrial fission without added stress. (FIG. 10C) Aberrant cytoplasmic localization sensitizes cells to ROS. Yeast cells with the indicated genotypes were treated with low dose $H_2O_2$ as indicated. Mid-log cultures before and after ROS stress were diluted 1:10 then spotted on growth medium lacking $H_2O_2$.

(FIG. 11B) Representative images of MEF cells incubated with TAT-HAD peptide or control (25 μM) for three hours then fixed and stained for the nucleus (DAPI), mitochondria (MitoTracker Red) and cyclin C (α-cyclin C). Arrows indicate regions of interaction between cyclin C and mitochondria.

(FIG. 13A) Space filling model of cyclin C illustrating the HAD and hydrophobic Helix 2', 3' and 4' comprising the second cyclin box fold domain. The position of the yeast Ser266 on the loop between helix 3' and 4' is indicated. Cdk8 binding site is on the backside of this image. (FIG. 13B) Ribbon model rotated 90° with the same features described in (FIG. 13A).

FIGS. 14A-14D demonstrate that the cyclin C regulatory system is intact in HeLa cells. (FIG. 14A) cyclin C localization in H2O2 stressed cultures as indicated. See (FIG. 14B) for enlarged images for 6 hr+$H_2O_2$ cells. (FIG. 14C) Knockdown efficiency of cyclin C by siRNA. con=scrambled siRNA control. Annexin V studies in the cultures described in (FIG. 14D). Graph illustrates % annexin V positive cells for cells with and without Cyclin C siRNA knockdown in the presence or absence of $H_2O_2$. Error bars=s.e.m. Three independent cultures were assayed for each sample.

FIGS. 15A-15C demonstrate cyclin C regulation in breast cell lines. (FIG. 15A) cyclin C localization was followed in MCF-7 or MCF-10A cells exposed to $H_2O_2$ (0.4 mM) for 4 h. (FIG. 15B) cyclin C levels were monitored by Western blot in MCF-7 cells treated with (+) or without (−) CCNC specific siRNAs. β-tubulin levels were followed as a loading control. (FIG. 15C) Viability was measured (viable stain assays) in the cell lines described in (FIG. 15B) following 4 h $H_2O_2$ exposure as indicated.

DETAILED DESCRIPTION OF THE INVENTION

Figure 1A:
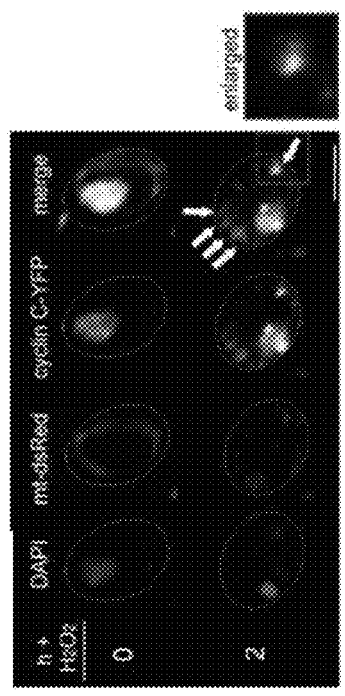
FIGS. 1A-1E provide stress-induced mitochondrial localization of cyclin C.
Figure 1B:
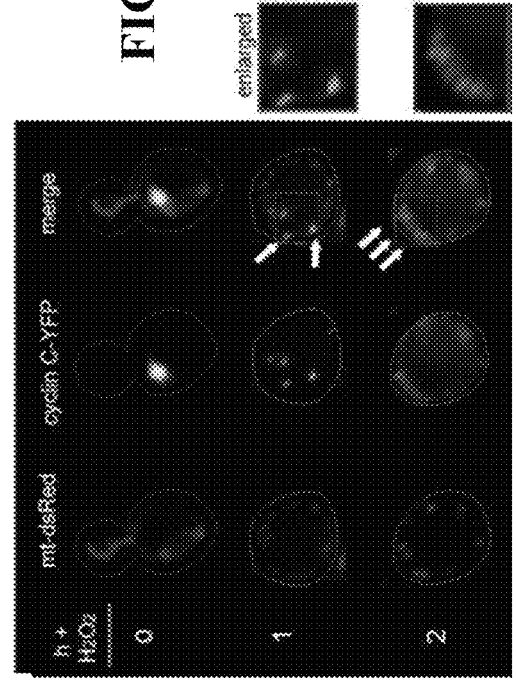
Figure 1C:
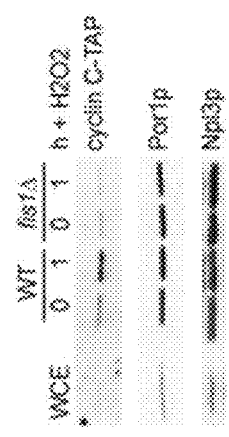
Figure 1D:
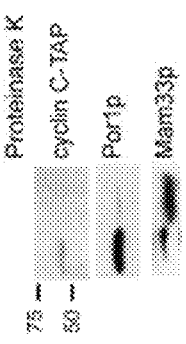
Figure 1E:
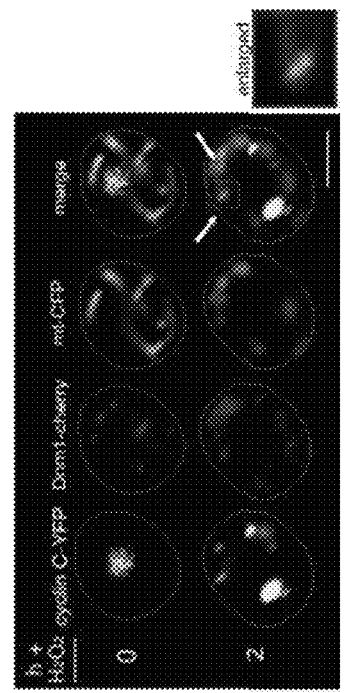

In at least one aspect of the present invention, the inventors provide evidence that, prior to its destruction, cytoplasmic cyclin C interacts with the fission machinery to promote stress-induced mitochondrial hyper-fission. These findings indicate that stress induced gene induction and mitochondrial fission are coordinated through cyclin C relocalization.

Mitochondrial morphology is controlled by the opposing activities of the fusion and fission machinery. In many organisms tested, cellular damage results in a dramatic shift in mitochondrial morphology from highly interconnected tubules to extensive fragmentation. Failure to undergo elevated fission reduces the ability of the cell to survive exogenous stress. Although the same machinery is required for normal and stress-induced fission, how the cell shifts the balance toward fission has remained enigmatic. In at least one embodiment, the present inventors first provide evidence that the nuclear transcription factor cyclin C is both necessary and sufficient to induce extensive mitochondrial fragmentation. Cyclin C and its kinase Cdk8p negatively regulate a subset of stress response genes.

In response to stress, this repression is relieved by cyclin C relocalization to the cytoplasm where it is destroyed. Prior to its destruction, cyclin C interacts with Mdv1p and is required for stress-enhanced Mdv1p-Dnm1p association. As such, the inventors successfully show a new mechanism that coordinates stress gene induction with mitochondrial fission through cyclin C function.

In another aspect of the invention, the inventors describe the mechanism by which cyclin C enhances mitochondrial fission in stressed cells. In one embodiment, it is contemplated provided that the cyclin C-Cdk8p kinase regulates the transcription of genes which control the fission/fusion balance. In at least another embodiment, it is shown that cyclin C plays a cytoplasmic role, independent of Cdk8p, to mediate mitochondrial fission.

In at least one aspect of the invention, inventors provide several pieces of data indicating that loss of cyclin C does not alter mitochondrial morphology in unstressed cells. Previous studies have demonstrated that reducing or overexpressing components of the fission or fusion machinery changes mitochondrial fission under normal growth conditions (Bleazard et al., 1999; Hermann et al., 1998; Otsuga et al., 1998; Sesaki and Jensen, 1999). In addition, the HADΔ mutation causes loss of transcriptional repressor ability (Cooper and Strich, 1999). However, contrary to the general understanding in the art, the strains harboring the cnc1A allele, cyclin $C^{HAD\Delta}$ enhances, rather than preventing fission. Finally, the presence of the A110V mutation still permits cyclin C transcriptional regulation but prevents its translocation to the cytoplasm (Cooper et al., 2012).

In another aspect of this invention, it is demonstrated that cyclin –$C^{A110V}$ can no longer mediate stress-induced fission. As such, the inventors for the first time provide that it is a cytoplasmic, not a transcriptional role for cyclin C that contribute and regulate mitochondrial fission.

Figure 6A:
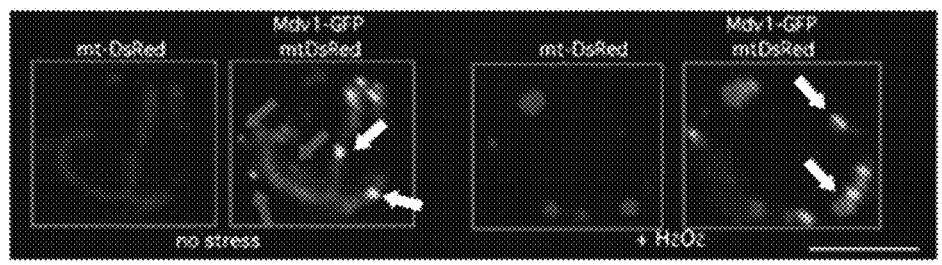
FIGS. 6A-6F further show that stress-induced Mdv1p mitochondrial localization requires cyclin C.
Figure 6B:
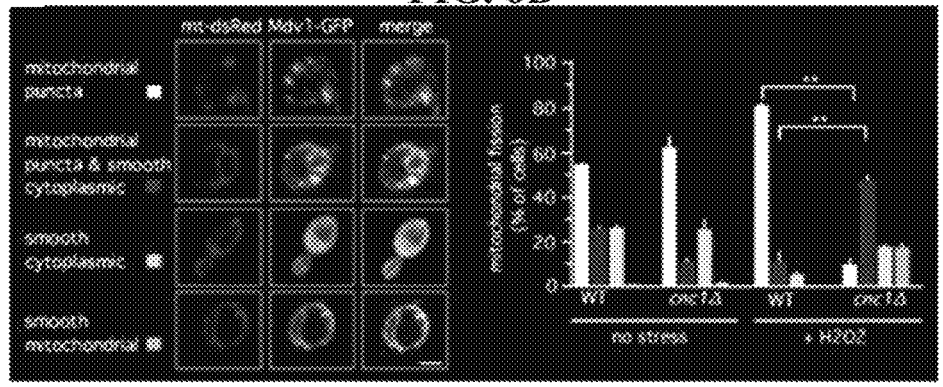
Figure 6C:
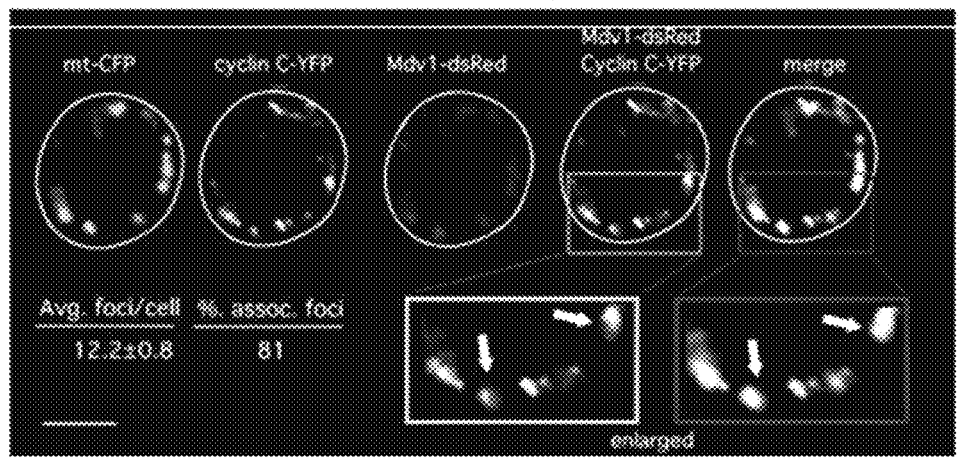
Figure 6D:
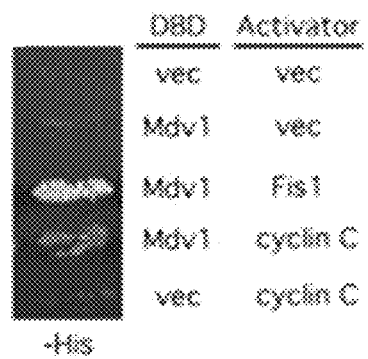
Figure 6E:
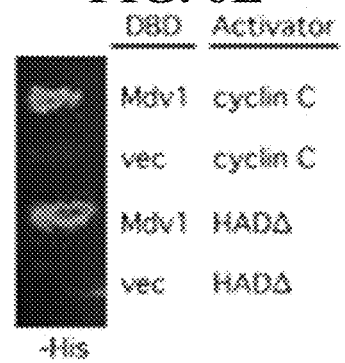
Figure 6F:
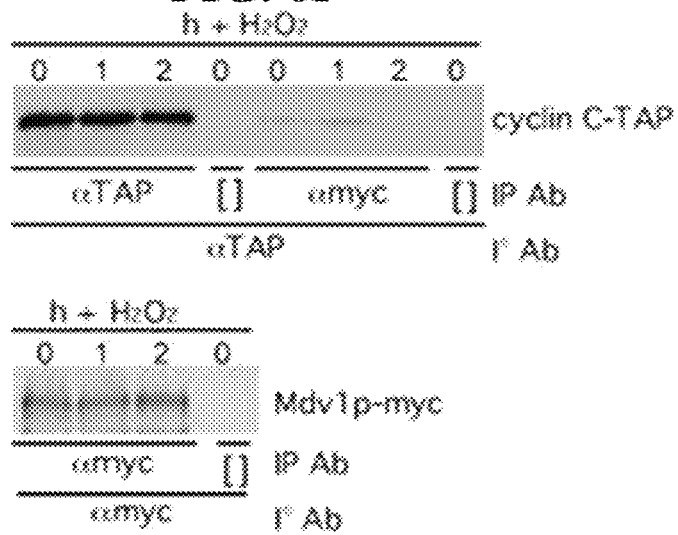
Figure 6G:
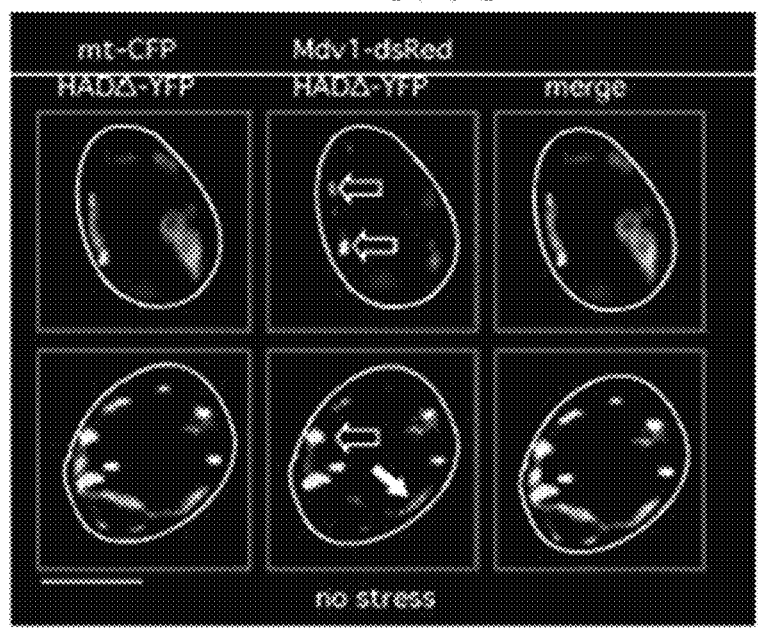
(FIG. 6G) A wild-type strain expressing mt-CFP, cyclin $C^{HAD\Delta}$-YFP and Mdv1p-dsRed was grown to mid-log phase then examined by fluorescence microscopy. The arrows indicate areas of co-localization between the two proteins and the mitochondria.
Figure 7A:
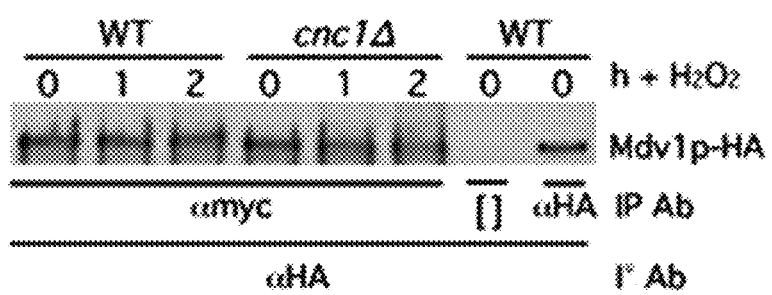
FIGS. 7A-7D provide that Cyclin C is required for stress-elevated Dnm1p-Mdv1p interaction.
Figure 7B:
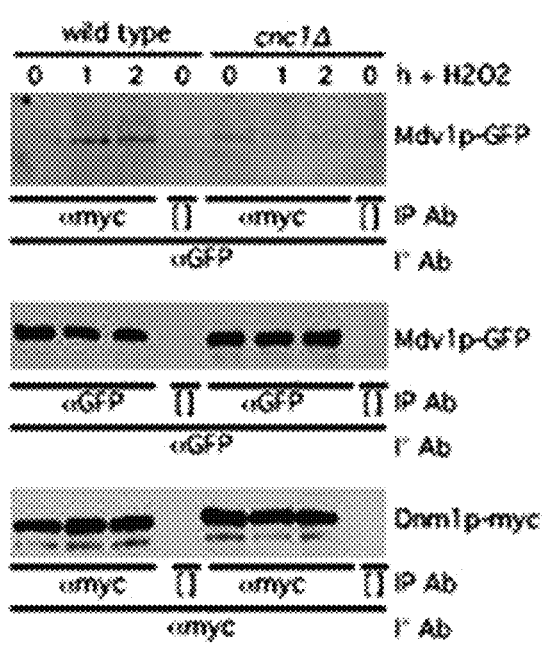
Figure 7D:
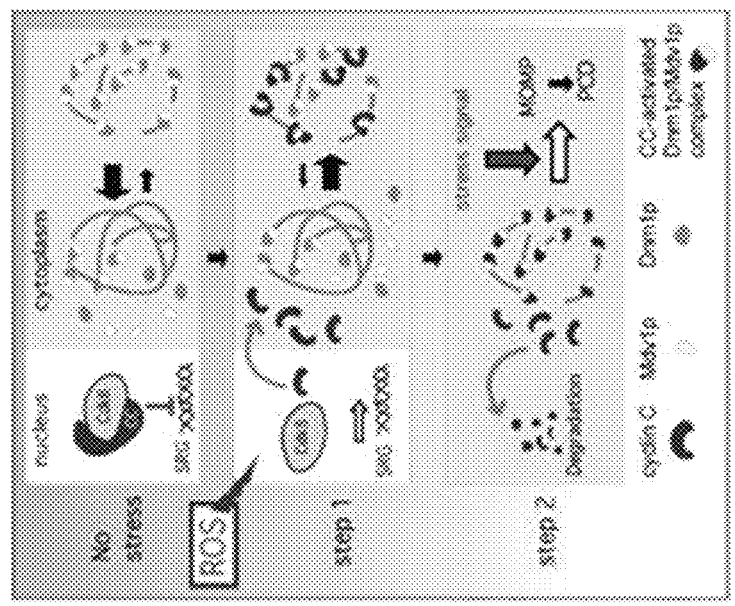
Figure 7C:
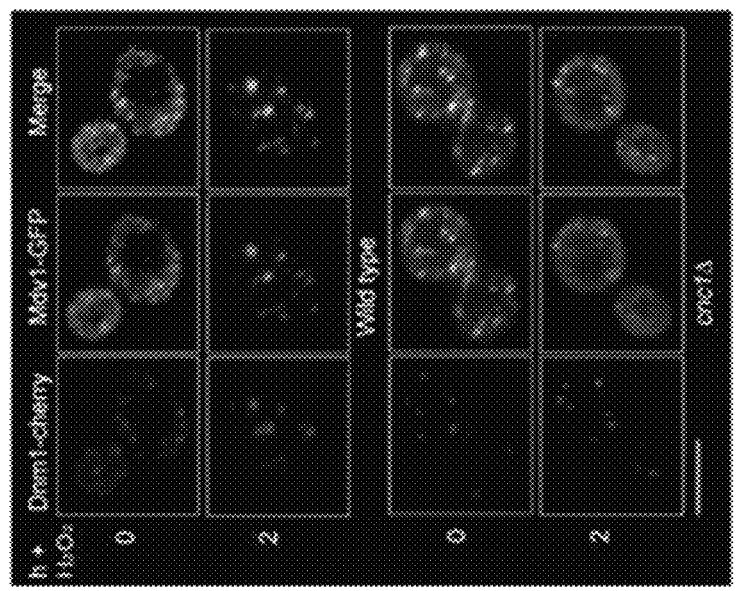

In unstressed wild-type cells, the majority of Dnm1p is assembled into inactive aggregates located on the sides of mitochondria (Legesse-Miller et al., 2003; Schauss et al., 2006). However, in response to stress, Dnm1p foci are predominately in the "activated" state as defined by their centered location on the mitochondrial axis and the appearance of a membrane constriction at this site (see FIG. 6A). Whether these "activated" foci are converted from inactive aggregates or are generated de novo can further be proven significant, although the latter seems more likely. In either case, the appearance of "active" Dnm1p foci is not observed in stressed cnc1Δ mutants indicating that the cyclin is required for this critical step in the fission process. A similar phenotype was observed in mdv1Δ mutants suggesting a functional interaction between these two proteins.

In another embodiment, the present inventors provide three independent methods that cyclin C and Mdv1p physically interact. The results from these methods suggest that cyclin C stimulates, and/or stabilizes, an elevated interaction between Mdv1p and Dnm1p that in turn promotes stress-induced mitochondrial fragmentation.

In another aspect, the present inventors identify the regulatory role of cyclin C in promoting stress-induced mitochondrial fragmentation. In one embodiment, it has been observed that the number of cyclin C molecules in the cell is greatly reduced compared to Dnm1p or Mdv1p. For the latter two proteins, their estimated abundance is approximately 9600 and 3700 molecules per cell based on Western blot analysis probing for identical epitope tags (Ghaemmaghami et al., 2003). However, the same study did not detect cyclin C (or Cdk8p) in their assays suggesting a far smaller concentration as is typical for many transcription factors. In addition, the co-immunoprecipitation experiments as provided herein found that the cyclin C-Mdv1p interaction was detected predominately early in the stress timecourse. However, this interaction was transient being somewhat reduced by 2 h post $H_2O_2$ addition. This is an unexpected observation as these results were not anticipated as the interaction of cyclin C-YFP and Mdv1p-Cherry is clearly observed at this latter timepoint.

Given the stringent conditions employed in these co-immunoprecipitation experiments compared to imaging live cells, these observations highlights differences in complex stability early and late in the oxidative stress response. Interestingly, the Mdv1p-Dnm1p interaction observed in stressed cells remained elevated through the two hour timepoint well within the timeframe in which mitochondrial fission is actively ongoing. Taken together, these results suggest a model that cyclin C is required early in the process to establish productive Fis1p-Mdv1p-Dnm1p complexes capable of executing a scission reaction. It is for the first time, that the present inventors provide that loss of cyclin C from this complex, and its subsequent destruction, represent a new mechanism by which the cell attenuates this accelerated mitochondrial fission process. Alternatively, but not mutually exclusive, unlike fis1Δ mutants, loss of cyclin C activity does not alter mitochondrial morphology in unstressed cells. Therefore, more reticular mitochondria, unlike the aggregates observed in fis1Δ mutants, may provide alternate way to deal with ROS-induced cell damage. Taken together, these new observations lend themselves to a new therapeutic target for patients suffering from hyperproliferative pathophysiological conditions that can benefit from an accelerated mitochondrial fission process.

The present inventors have found that cyclin C, a nuclear transcription factor, has a critical second function in promoting both stress-induced mitochondrial fission and the intrinsic programmed cell death (PCD) response. One important finding is that when cyclin C leaves the nucleus and associates with the mitochondria, it triggers both fission and PCD. In view of this, therapeutic approaches are described that may be used to manipulate cyclin C localization to selectively enhance tumor sensitivity to intrinsic reactive oxygen species (ROS) and/or anti-cancer drugs.

Unlike other cyclin-Cdks that control the cell cycle, cyclin C, and its cyclin dependent kinase Cdk8, regulate transcription through direct association with the RNA polymerase II holoenzyme. The present inventors have identified a second function for cyclin C that occurs outside the nucleus. When mouse embryonic fibroblasts (MEFs) or human tumor cell lines are subjected to oxidative stress or the anti-cancer drug cisplatin, a portion of cyclin C translocates from the nucleus to the cytoplasm where it triggers the extensive mitochondrial fragmentation observed in damaged cells. In addition, using knockout ($CCNC^{-/-}$) MEF cultures, it has been found that cyclin C is required for both mitochondrial fission and MOMP induction. The role cyclin C plays in PCD appears to be specific for the intrinsic mitochondrial pathway as $CCNC^{-/-}$ MEF cells respond normally to death receptor mediated cell killing. The role cyclin C plays in promoting both mitochondrial fission and PCD is independent of its kinase partner Cdk8 and is conserved from budding yeast to humans.

The present inventors have found that introducing cyclin C into the cytoplasm of permeabilized MEF cells is sufficient to induce mitochondrial fission in the absence of stress. Similarly, deleting its nuclear anchor (Med13p) in yeast, cyclin C not only enters the cytoplasm and induces fission, but also makes the cells hypersensitive to oxidative stress. The addition of a membrane permeable peptide mimetic is shown to be sufficient to disrupt cyclin C-Med13 interaction in mouse cells in vitro, releasing cyclin C into the cytoplasm, and inducing extensive mitochondrial fragmentation. While not intending to be bound by any theory of operation, it appears that pharmacologically induced release of cyclin C into the cytoplasm is capable of both stimulating mitochondrial fission and reducing the toxic threshold to ROS. Since oxidative stress is already markedly elevated in cancers, such an approach is likely to preferentially target tumors.

In certain embodiments, there are provided compounds and methods for inducing the nuclear to cytoplasmic translocation of cyclin C. In certain embodiments, there are provided compounds and methods for disrupting the interaction of cyclin C with the RNA polymerase II holoenzyme component Med13.

In certain embodiments, the compound is defined as an agent that binds the alpha helical domain of the full length human cyclin C within amino acids 1-16 and/or 18-29, which results in disruption of its interaction with the RNA polymerase II holoenzyme component Med13.

In embodiments, the compound will associate with the HAD domain interacting region on Med13, resulting in disruption of this interaction. Released cyclin C is then translocated from the nucleoplasm to the cytoplasm via an unspecified export mechanism. In the cytoplasm, cyclin C associates with, and then enhances, the activity of the mitochondrial fission protein Drp1 to simulate fragmentation of this organelle. This hyper fragmented state lowers the threshold required by reactive oxygen or other inducers of cellular damage required to activate the programmed cell death pathway.

In certain embodiments, there is provided a method of inhibiting tumor growth or sensitizing a tumor cell to a therapeutic agent comprising contacting a tumor cell with a compound capable of disrupting the interaction of cyclin C with the RNA polymerase II holoenzyme component Med13. In embodiments, the compound comprises the holoenzyme association domain (HAD) of cyclin C or a fragment or variant thereof. In embodiments, the HAD, fragment or variant thereof has an activity comprising inducing the translocation of cyclin C from the nucleus to the cytoplasm. In embodiments, the molecule may be a peptide or mimetic, including a small molecule.

In embodiments, the molecule may further comprise a promoter of cellular membrane translocation. In embodiments, the promoter of translocation may be an amino acid sequence capable of promoting cellular membrane translocation. In certain embodiments, the HIV TAT translocation sequence YGRKKRRQRRR (SEQ ID NO:1) may be used. Other amino acid sequences may be used, including, but not limited to Penetratin [RQIKIWFQNRRMKWKK] (SEQ ID NO:2); and FHV [RRRRNRTRRNRRRVR] (SEQ ID NO:3).

In embodiments, a pharmaceutical composition is provided comprising a peptide or peptide mimetic comprising the holoenzyme association domain (HAD) of cyclin C or a fragment or mimetic thereof. In embodiments, the pharmaceutical composition may further comprise at least one further active agent. Suitable further active agents may be anti-cancer agents. Such anti-cancer agents include an anti-angiogenesis agent, selective estrogen-receptor modulator (SERM), breast cancer therapeutic agent, aromatase inhibitor, biologic response modifiers, hormonal therapies agent, anthracycline, taxane, alkylating agent, taxol, cisplatin, arabinofuranosyl cytosine (ara-C), 5-fluorouracil (5-FU), altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, goserelin acetate, fulvestrant, doxorubicin, epirubicin, or cyclophosphonamide and the like. More preferred anti-cancer agents may include cisplatin, paclitaxel, etoposide, aminolevulinic acid, bleomycin, doxorubicin, and tamoxifen.

In at least another embodiment, an amino acid sequence capable of promoting cellular membrane translocation may be conjugated to the anti-cancer agent directly or via a hydrolysable linker.

Another embodiment provides a pharmaceutical kit comprising a container, a pharmaceutical composition described herein and instructions for using the pharmaceutical composition to treat a disease or condition in a mammal.

Other embodiments provide a compound for use in anti-cancer treatment comprising a peptide sequence comprising the holoenzyme association domain (HAD) of cyclin C or a fragment or mimetic thereof. In certain embodiments, the compound further comprises a promoter of cellular membrane translocation. In embodiments, the promoter of translocation may be an amino acid sequence capable of promoting cellular membrane translocation. In certain embodiments, the HIV TAT translocation sequence YGRKKRRQRRR (SEQ ID NO:1) may be used. Other amino acid sequences, including, but not limited to Penetratin [RQIKIWFQNRRMKWKK] (SEQ ID NO:2), and FHV [RRRRNRTRRNRRRVR] (SEQ ID NO:3) may be used.

In embodiments, the compound comprises the amino acid sequence KERQKDL (SEQ ID NO:4), which is part of the HAD of cyclin C. In embodiments, the compound comprises the peptide sequence WILDKQDLLKERQKDL (SEQ ID NO:5) of the cyclin C HAD (FIG. 11A) or a fragment or variant thereof. In embodiments, the peptide, fragment or variant thereof has an activity comprising inducing the translocation of cyclin C from the nucleus to the cytoplasm. In embodiments, the peptide comprises at least 14 amino acids.

Figures 11A, 11B:
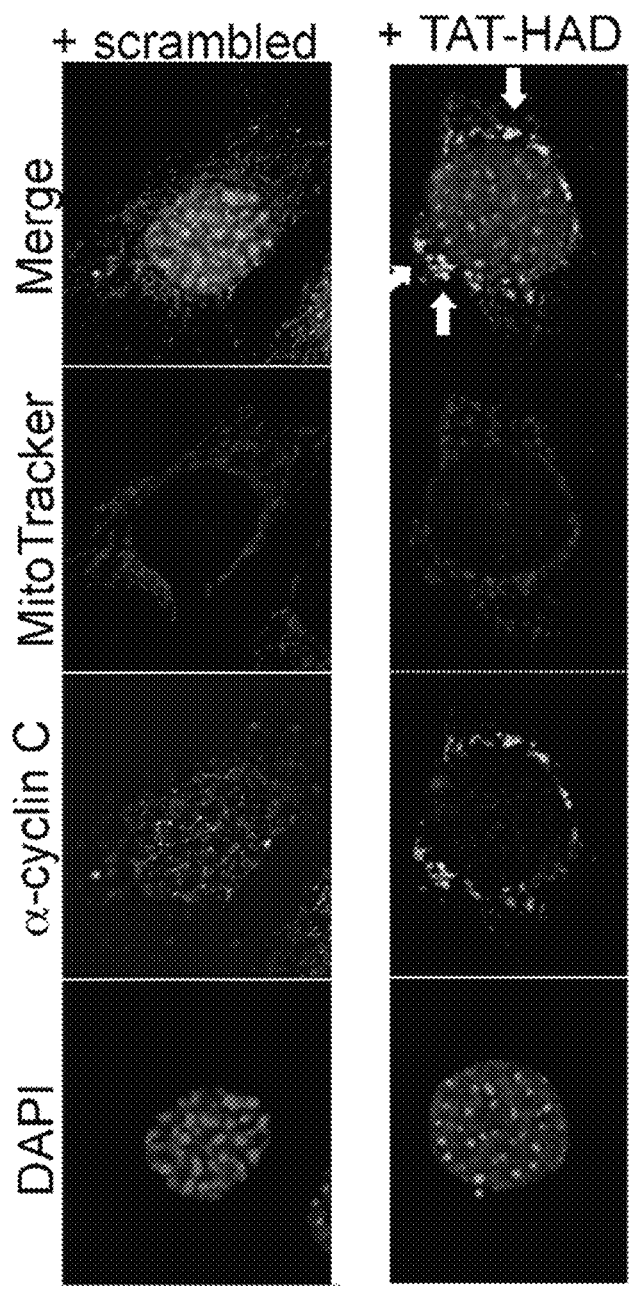
FIGS. 11A-11B demonstrate the disruption of the holoenzyme association domain (HAD)-Med13 interaction. The amino terminal sequences of cyclin C from the indicated organisms. Homologies are shaded. Boxed region is targeted using the HIV TAT basic domain fused to the 19 amino acid (aa) peptide indicated by the line above the sequence.

In certain embodiments, the compound comprises the TAT-HAD peptide shown in FIG. 11A, having amino acid sequence YGRKKRRQRRRWILDKQDLLKERQKDL (SEQ ID NO:6). In embodiments, the peptides may have an overall length of up to 100, amino acids, preferably up to 50, 30 and more preferably up to 22 amino acids. In embodiments, the compound may comprise derivatives or variants of the above amino acid sequences. In embodiments, the sequences described may be modified to optimize activity.

While not intending to be bound by any theory of operation, stapled peptides may have several advantages over compounds such as the TAT-HAD described in FIG. 11B. Stapled peptides maintain their helical structure better, bind targets with higher affinity, demonstrate robust cell entry via endocytic pathways and are more stable in vivo compared to peptides that are not stapled (reviewed in, e.g., in Verdine, G. L. and G. J. Hilinski, Stapled peptides for intracellular drug targets, Methods Enzymol, 2012. 503: p. 3-33).

In at least one embodiment, the identified characteristics of successful stapled peptides have been identified. As such, preferably, the peptide is 10-30 amino acid residues in length and more preferably 18-22 amino acid residues in length. Preferably, the peptide has a charge ≥0. Preferably, the peptide has ≥60% alpha helical content. In at least one embodiment, the charge is 1, 5, 15, 20, 25, 30, 35, 40, 45 and 50. Preferably, the staple should be placed opposite of the interactive face of the helix.

Figure 12:
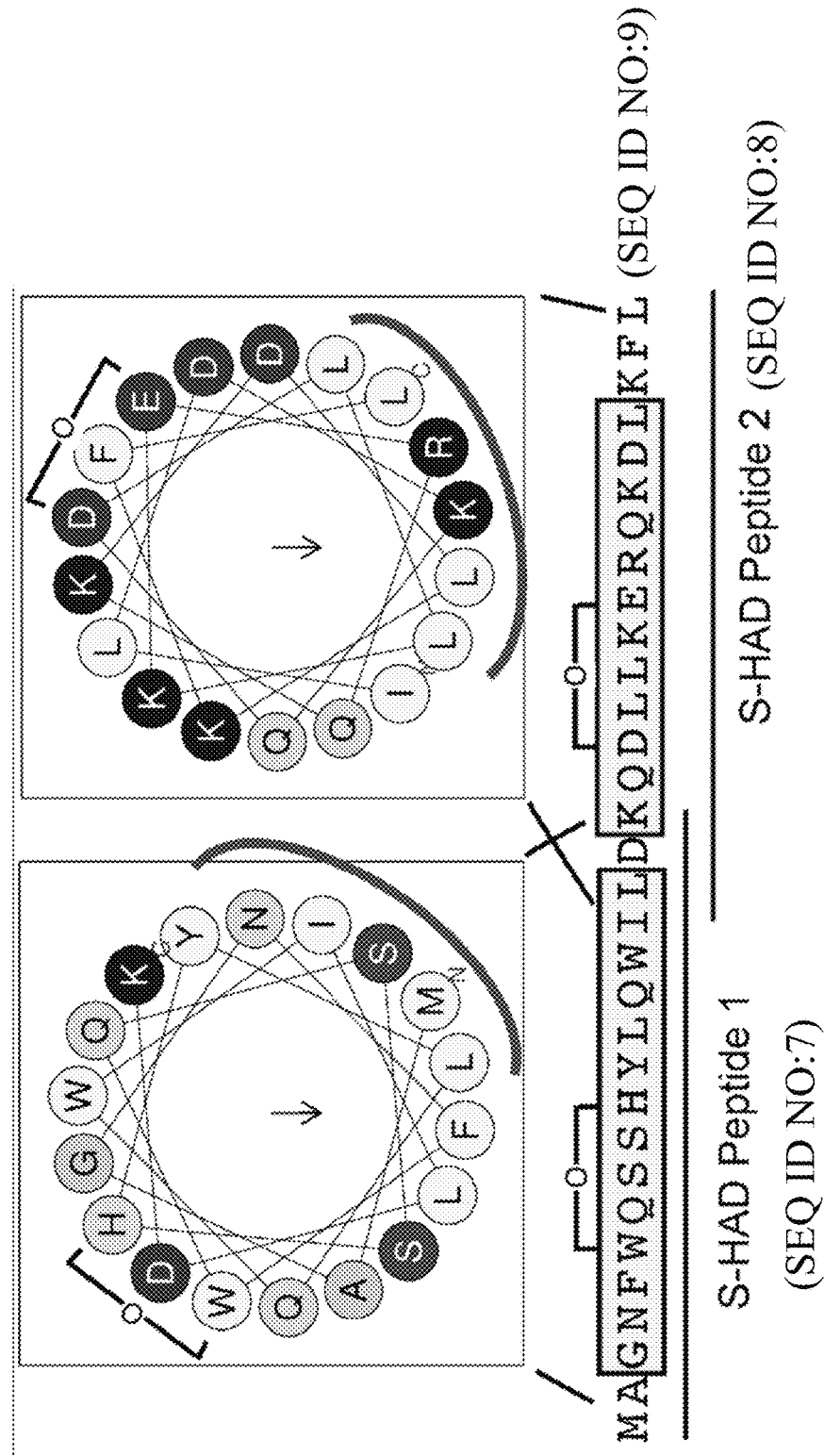
FIG. 12 shows the design of a stapled-HAD (S-HAD) peptide. The primary sequence of the human cyclin C HAD domain is presented. Boxes indicate alpha helix structures from both prediction algorithms and crystal structure analysis. Helical wheels generated from the Helix 1 or Helix 2 sequences are indicated. The start of each plot (n) and end (c) are indicated. Predictive interactive interfaces of the two alpha helixes indicated by the arc were derived from both RASMOL modeling and yeast genetic data. Initial sites for introducing staples are indicated on each helix and the primary sequence below.

Structural examination of the HAD has led to the identification of an alpha helical domain (Hoeppner, S., S. Baumli, and P. Cramer, Structure of the mediator subunit cyclin C and its implications for CDK8 function, J Mol Biol, 2005. 350(5): p. 833-42]; FIG. 12). It has been demonstrated that replacing the KERQK sequence (boxed, FIG. 11A) with alanines (HADA) or single amino acid substitutions that disrupt the α-helical structure (e.g., substitution of a proline for the leucine in the domain) also disrupts HAD function [Cooper, K. F. and R. Strich, Functional analysis of the Ume3p/Srb11p-RNA polymerase II holoenzyme interaction. Gene Expr, 1999. 8(1): p. 43-57; Cooper, K. F., S. Khakhina, S. K. Kim, and R. Strich, Stress-Induced Nuclear-to-Cytoplasmic Translocation of Cyclin C Promotes Mitochondrial Fission in Yeast. Dev Cell, 2014. 28: p. 161-173.]. While not intending to be bound by any theory of operation, these results indicate that the HAD is predicted to be helical in nature, and that a helical structure is important for its function. Closer inspection of the human HAD reveals an extended helical region may be divided into helices 1 and 2 (FIG. 12). The second helix is the target of the TAT-HAD described herein.

Addition of more basic residues has been shown to increase cellular uptake [Holub, J. M., J. R. Larochelle, J. S. Appelbaum, and A. Schepartz, Improved assays for determining the cytosolic access of peptides, proteins, and their mimetics. Biochemistry, 2013. 52(50): p. 9036-46.]. Also, altering where the stapled residues are inserted can affect the binding ability [Bird, G. H., W. C. Crannell, and L. D. Walensky, Chemical synthesis of hydrocarbon-stapled peptides for protein interaction research and therapeutic targeting, Curr Protoc Chem Biol, 2011. 3(3): p. 99-117]. The addition of more than one staple has also been shown to protect the peptide from proteolysis [Verdine, G. L. and G. J. Hilinski, Stapled peptides for intracellular drug targets. Methods Enzymol, 2012, 503: p. 3-33].

Figure 13A:
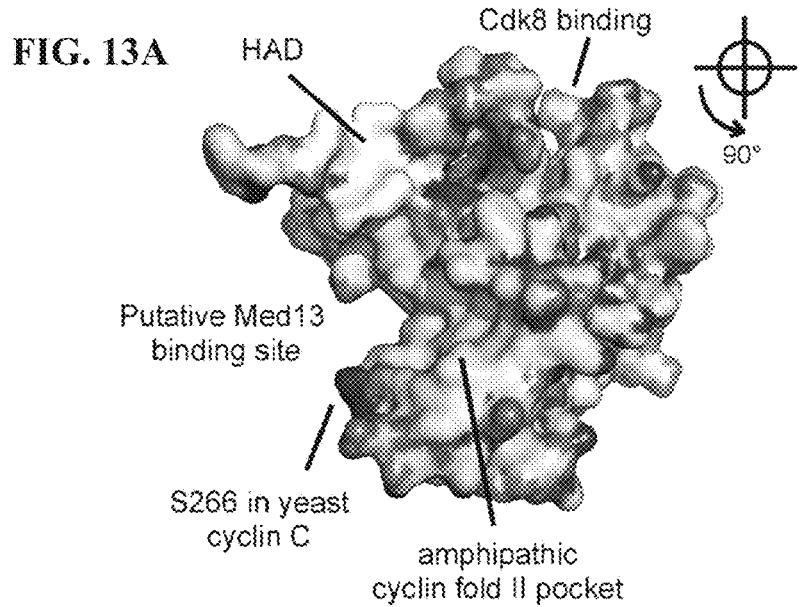
FIGS. 13A-13B show a proposed Med13 binding region on cyclin C.
Figure 13B:
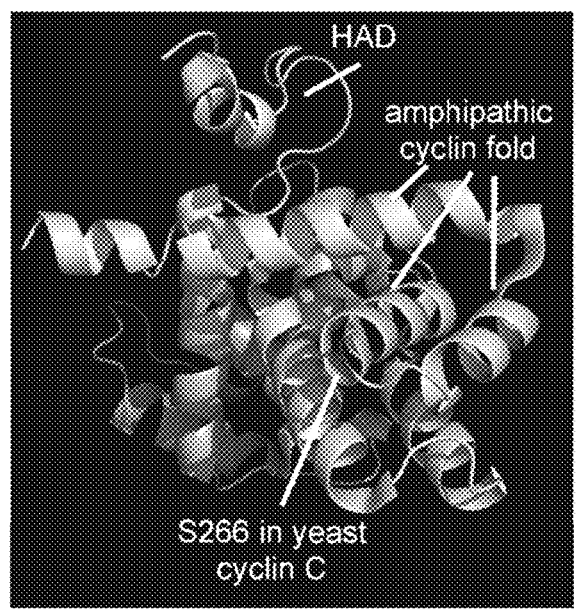

It has been found that phosphorylation of the yeast cyclin C on Ser266 destabilizes Med13p interaction [Jin, C., R. Strich, and K. F. Cooper, Slt2p phosphorylation is required for the stress-induced cytoplasmic translocation and destruction of the yeast transcriptional repressor cyclin C, Mol Biol Cell, 2014. In Press.]. Although this serine is not conserved in human cyclin C, it does provide structural cues to Med13 binding. When superimposed on the crystal structure of cyclin C, Ser266 is located at an exposed position flanking the second cyclin fold domain, between helix 3' and 4' (FIGS. 13A-13B). All cyclins contain two cyclin fold motifs. The first binds its cognate Cdk. The second motif has not been ascribed a function. These folds form an amphipathic pocket (hydrophobic residues, FIGS. 13A-13B) and represent a potential interaction site for Med13. Therefore, stapled peptides may be made directed to these hydrophobic surfaces.

In embodiments, a peptide is provided comprising SEQ ID NO:8, wherein the peptide comprises non-peptide bonds. In embodiments, the peptide comprises a crosslinked alpha-helical amino acid sequence comprising a crosslinker connecting a first amino acid to a second amino acid. The peptide preferably has an overall length of from 10-30 amino acids, and more preferably 18 to 22 amino acids.

In embodiments, the peptide may comprise derivatives or variants of the described amino acid sequences. In embodiments, the sequences described may be modified (e.g., changing the staple location, addition of more basic residue) to optimize activity.

While not intending to be bound by any theory of operation, it is believed that the peptide binds to Med13 in substantially the same way as a native polypeptide comprising the holoenzyme association domain of cyclin C.

In embodiments, compounds described herein comprise a peptide sequence, wherein the peptide sequence comprises cross-linking. In embodiments, the compound comprises a crosslinked alpha-helical amino acid sequence comprising a crosslinker connecting a first amino acid to a second amino acid. The crosslinker stabilizes an alpha-helix structure of the peptide. In embodiments, at least one of the amino acids of the peptide may be a non-natural amino acid. In embodiments, the cross-linked peptide has enhanced cell penetrability relative to a corresponding unmodified peptide.

In embodiments, a compound is provided comprising a crosslinked peptide comprising an alpha-helical domain of the holoenzyme association domain (HAD) of cyclin C. In an embodiment, the crosslinked peptide comprises two α-methyl, α-alkenglycine residues on the same side of the alpha helix.

In embodiments, also provided is a method of producing a peptide or mimetic described herein.

In embodiments, also provided is a non-human transgenic animal comprising a DNA construct capable of inactivating the expression of the endogenous CCNC gene.

In embodiments, also provided is a cell line comprising a cell wherein the expression of the endogenous CCNC gene has been inactivated.

Compounds as described herein may be capable of enhancing the sensitivity of tumor cells to reactive oxygen species and/or anti-cancer agents. In embodiments, compounds as described herein may be used in methods of treating cancer, comprising administering to a subject in need thereof a composition comprising the compound.

In certain embodiments, the present invention provides a method of treating a subject comprising administration of a composition. As used herein, the term "subject" is used to mean an animal, preferably a mammal, including a human. The terms "patient" and "subject" may be used interchangeably.

The therapeutic compositions may be administered by any route that delivers an effective dosage to the desired site of action, with acceptable (preferably minimal) side-effects. Numerous routes of administration of agents are known, for example, oral, rectal, transmucosal, or intestinal administration; parenteral delivery, including intramuscular, subcutaneous, intramedullary injections, as well as intrathecal, intraperitoneal, intranasal, cutaneous or intradermal injections; inhalation, and topical application.

Therapeutic dosing is achieved by monitoring therapeutic benefit and monitoring to avoid side-effects. Preferred dosage provides a maximum localized therapeutic benefit with minimum local or systemic side-effects. Suitable human dosage ranges for the polypeptides can be extrapolated from these dosages or from similar studies in appropriate animal models. Dosages can then be adjusted as necessary by the clinician to provide maximal therapeutic benefit for human subjects.

Cancer is a multi-step disease that includes the initial transformation event, progression and therapy resistance. Depending on the individual cancer examined, these steps require different inputs that are particular to the cell type (e.g., specific oncogene activation, tumor suppressor elimination) and from the microenvironment (e.g., extra cellular matrix composition) that affect tumor aggressiveness. The presence of tumor specific properties is well established and forms the basis for personalized anti-cancer therapy. Since cyclin C represents the first factor identified that regulates only hyper-fission but not normal mitochondrial division, it may be used to identify the spectrum of drug-cell type combinations that this factor controls.

While not intending to be bound by any theory of operation, given the ROS hypersensitivity observed in yeast when the mitochondrial are aberrantly fragmented, and the unusually high oxidative stress load experienced by many tumor types, it is possible that the peptides or peptide mimetics described herein may be used alone to reduce cell viability in tumor cells.

It is contemplated that the LD50 concentrations of certain chemotherapeutic drugs may be reduced in the presence of the cyclin C peptides/mimetics described herein.

In other embodiments, a method is provided for identifying the anti-cancer agent(s) whose action may be susceptible to enhancement by cyclin C translocation from the cell nucleus to the cytoplasm. As described herein, cyclin C translocation may be induced by administration of peptides or peptide mimetics that disrupt cyclin C-Med13 interaction. In embodiments, screening methods are provided to determine whether a given tumor cell type may be treated with a cyclin C peptide or peptide mimetic and a particular anticancer agent.

In an embodiment, a method is provided for identifying a combination of a tumor cell type and an anti-tumor agent whose action is susceptible to enhancement by cyclin C translocation. In embodiments, the method may comprise obtaining separate samples of tumor cells of a particular origin. The tumor cells may be obtained from any number of sources, including, but not limited to, tissue or cell culture banks, biopsies or samples obtained from patients. In embodiments, each sample is contacted with a different concentration of an anti-tumor agent. At least one control sample that is contacted with no anti-tumor agent may be included. The extent of mitochondrial fragmentation is determined in each sample. This determination may be quantitative. This determination may be performed using any suitable detection process, including, but not limited to, fluorescence microscopy. In embodiments, the release of cyclin C from the nucleus into the cytoplasm may be monitored in the samples by indirect immunofluorescence. Each tumor cell sample may be quantitatively analyzed using at least one marker of PCD to determine the percent of cells that are killed by each concentration of agent. The measurements of cell deaths are used to determine the LD50 for the anti-tumor agent with respect to the tumor cell type. The above steps are repeated in the presence of multiple compound concentrations that induce cyclin C translocation from the cell nucleus to the cytoplasm. Once active concentrations are obtained that induce cyclin C relocalization, the LD50 for the anti-tumor agents described in the control experiments are determined in the presence of the cyclin C compound, wherein a reduction in the LD50 of the anti-cancer agent signifies that the anti-cancer agent is susceptible to enhancement of its activity by cyclin C translocation. In embodiments, the screening methods described herein may be used by healthcare providers and patients in making improved treatment choices.

In an embodiment, a method is provided for identifying a combination of a tumor cell type and an anti-tumor agent whose action is susceptible to enhancement by cyclin C translocation, comprising: a) contacting separate samples of a tumor cell type with differing concentrations of an anti-tumor agent; b) measuring each tumor cell sample using at least one marker of programmed cell death to determine the percent of cells that are dead; c) using the measurements of cell deaths to determine the LD50 for the anti-tumor agent; d) repeating the above steps a-c in the presence of a compound that induces cyclin C translocation from the cell nucleus to the cytoplasm; and e) comparing the LD50 for the anti-tumor agent in the presence and absence of the cyclin C compound, wherein a reduction in the LD50 of the anti-cancer agent indicates that the agent is susceptible to enhancement of its activity by cyclin C translocation.

In embodiments, the compound that induces cyclin C translocation may be a peptide or a peptide mimetic, as described herein.

Any suitable anti-cancer agent may be used. In embodiments, the anti-cancer agent may be selected from the group including, but not limited to, cisplatin, paclitaxel, bleomycin, doxorubicin, and tamoxifen.

In embodiments, the tumor cell may be selected from the group including, but not limited to, lung, mammary, melanoma, ovarian, prostate and kidney tumor cells.

The following examples serve to further illustrate the present invention.

EXAMPLE 1:

Materials and Methods
Strains and Plasmids

The strains used in this study are derived from a W303α-related strain RSY10 (Strich et al., 1989) and listed in the Supplemental Materials and methods section. In accordance with the mediator nomenclature unification effort (Bourbon et al., 2004), the yeast cyclin C-Cdk8p kinase will use CNC1 (a.k.a. SSN8/SRB11/UME3) and CDK8 (a.k.a. SSN3/SRB10/UME5) gene designations, respectively. Please see Supplemental Materials and methods section for details about plasmids used in this study.

Cell Growth and Survival Assays

Cells were grown in either rich, non-selective medium (YPDA) or synthetic minimal medium (SC) allowing plasmid selection as previously described (Cooper et al., 1997). Galactose inducible gene expression (gal1-mt-CFP and MDV1-dsRed) was achieved by adding galactose (1% final concentration) to cultures grown in SC with raffinose as the carbon source. All MET25 inducible plasmids (MDV1-MYC, MDV1-HA, FIS1-MYC) were grown under non-inducing conditions as described (Koirala et al., 2010). Viability studies were conducted with mid-log phase ($6 \times 10^6$ cells/ml) treated with 1 or 2 mM $H_2O_2$ for 2 h then serially diluted (1:10) and plated on minimal complete medium with or without plasmid selection as indicated in the text. TUNEL assays were conducted essentially as previously described (Krasley et al., 2006; Madeo et al., 1997). At least 400 cells were counted per timepoint from three independent cultures. DHE oxidation assays were performed as described (Buttner et al., 2007) and DHE positive cells were quantitated by direct cell count using fluorescence microscopy. All statistical analysis was performed using the student's T test with p<0.05 considered significant. All analyses were conducted with at least three independent cultures with 200 or more cells counted per timepoint.

Subcellular Fractionation

Subcellular fractionation of yeast mitochondria were accomplished essentially as described previously (Diekert et al., 2001) with the following modifications. The enriched mitochondrial fraction was purified from a mid-log phase culture (4 L per timepoint) before and one hour after treatment with $H_2O_2$ (1 mM). Due to the low abundance of cyclin C-TAP, approximately one third of the enriched mitochondrial preparation was loaded per sample. Whole cell extract samples represent 1/100 of mitochondrial preparation. Proteinase protection assays of mitochondrial bound cyclin C were conducted by adding 100 µg/ml of recombinant Proteinase K (Roche) for 15 min on ice. The control sample was incubated under the same conditions without added protease.

Immunofluorescence Microscopy

Localization studies of chimeric fusion proteins were performed on fixed or living cells as indicated in the text. Cells were fixed in 3.7% para-formaldehyde and stained with 4', 6-diamidino-2-phenylindole (DAPI). For all experiments, the cells were grown to mid-log ($5\times10^6$ cells/nil), treated with 1 mM $H_2O_2$ for the timepoints indicated, then analyzed by fluorescence microscopy as described in the Supplemental Materials and methods. The images (0.2 µm slices at 0.2 µm spacing) were analyzed as described above. In all panels, the bar=5 µm unless otherwise stated.

Fluorescence Microscopy Scoring Methods

Figure 2G:
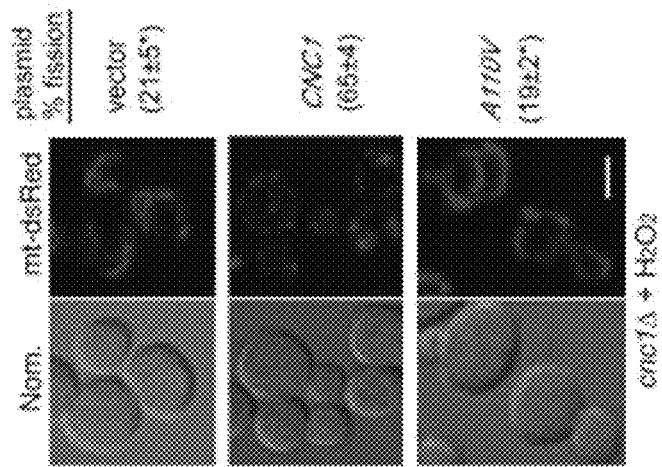
Figure 2F:
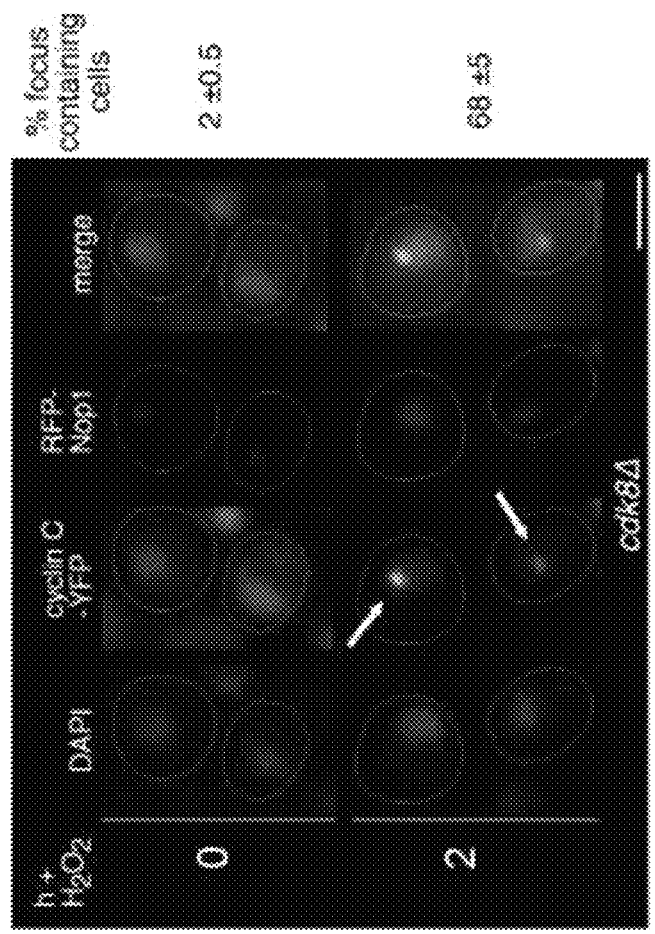
Figure 4A:
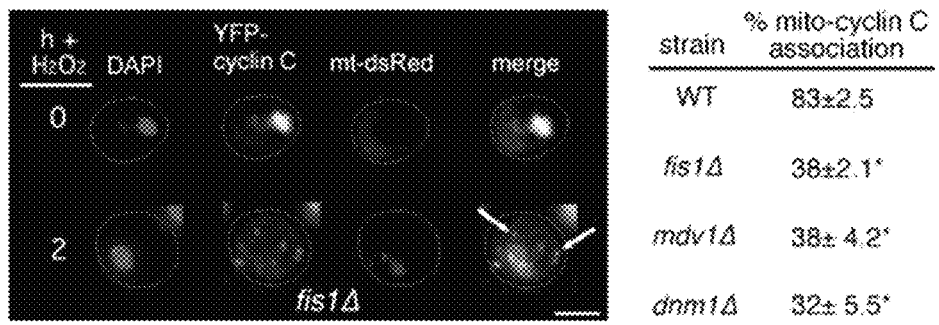
FIGS. 4A-4D provide that mitochondrial localization of cyclin C requires the fission complex.
Figure 4B:
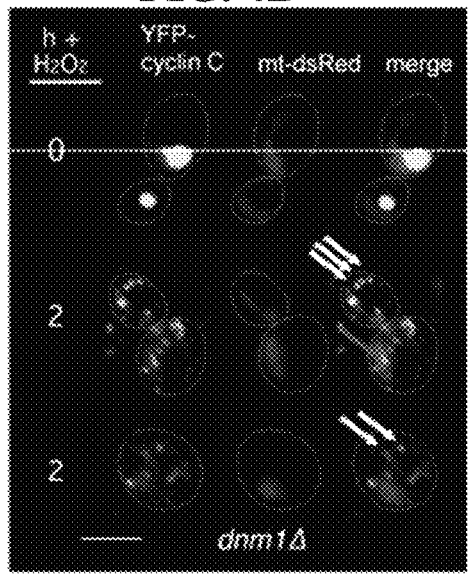
Figure 4C:
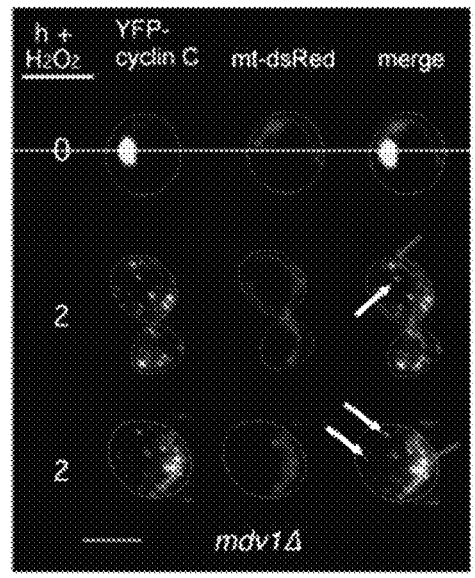
Figure 4D:
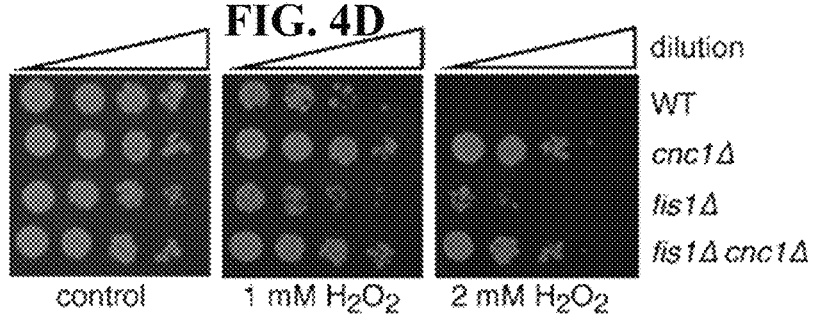
Figure 5B:
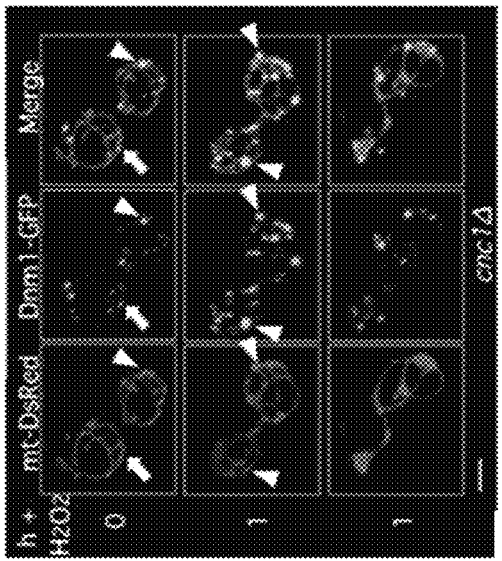
FIGS. 5A-5C provide that Cyclin C is required for functional Dnm1p filament formation. Dnm1p-GFP subcellular localization was visualized by confocal microscopy before and following $H_2O_2$ stress (1 mM) for the times indicated in (FIG. 5A) WT, (FIG. 5B) cnc1Δ or (FIG. 5C) mdv1Δ cells harboring Dnm1p-GFP and mt-DsRed plasmids. Arrows indicate functional Dnm1p-GFP foci as determined by their centered location with respect to the mitochondrial axis and the constriction of the mitochondrial diameter. Arrowheads indicate non-functional aggregates as indicated by their association with the edge of the mitochondria and the lack of mitochondrial constriction.
Figure 5D:
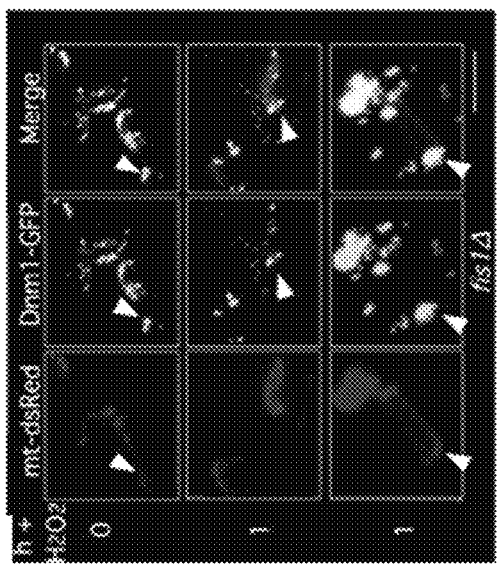
Figure 5A:
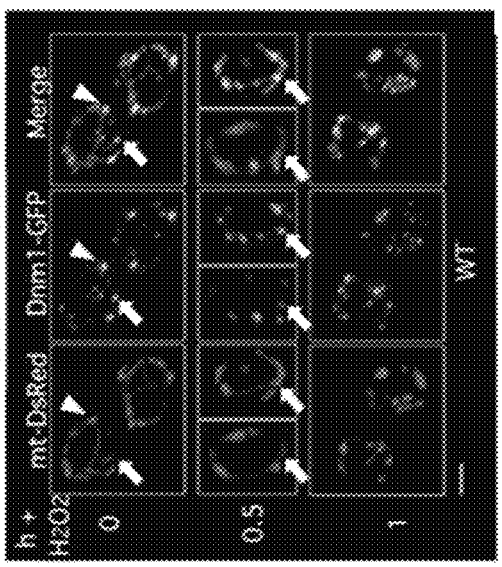
Figure 5C:
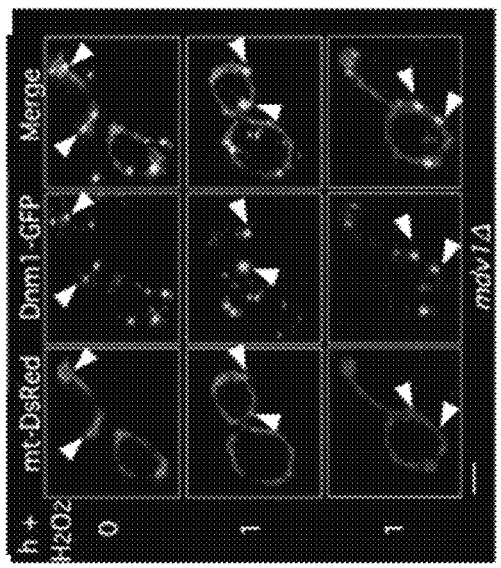

To measure co-localization signals (FIGS. 1E, 4A, 4B, 4C, 6C, 7B, 7C), total foci exhibiting co-localization (with the mitochondria or another protein signal) were divided by the total foci observed. At least 30 cells were counted from three independent samples. Mitochondrial fission was scored positive if no reticular mitochondria were observed that transversed half the cell diameter. Fusion was scored when cells exhibited one or more reticular mitochondria the diameter of the cell. Fission and fusion was scored for 200 cells from three independent isolates. The intermediate or mixed mitochondria phenotype (FIG. 3C) described cells containing both ≥3 mitochondrial fragments in addition to an elongated mitochondrion equal to the diameter of the cell. The cyclin C-YFP-nucleolus association (FIG. 2D) was scored positive when one condensed YFP signal was observed within or adjacent to the nucleolar signal. 50 cells were counted from three independent isolates. Statistical analysis was performed using the Student's T-test with p<0.05 used to indicate significant differences.

Molecular Biology Methods

Western blot and co-immunoprecipitation analyses from yeast extracts were performed essentially as described (Cooper et al., 1997) with the modifications indicated in the Supplemental Materials and methods include Western blot signals detected using secondary antibodies conjugated to alkaline phosphatase (Sigma) and the CDP-Star chemiluminescence kit (Tropix). Quantitation of Western blot signals was accomplished using the chemiluminescence imager (Kodak Inc.).

EXAMPLE 2:

Materials and Methods

U2OS and Hela cells were obtained from ATCC and were cultured in in Dulbecco's modified Eagle's medium (DMEM) supplemented with 10% fetal bovine serum (FBS) and 1% penicillin/streptomycin. For localization and mitochondrial morphology experiments in MEF cultures, the cells were maintained in 5% $CO_2$, 5% $O_2$. $CCNC^{+/+}$ and $CCNC^{fl/fl}$ MEF cell lines were established from 13.5 dpc embryos using standard protocols. These cell lines were subsequently immortalized through introduction of the SV40 T antigen. The immortalized $CCNC^{fl/fl}$ MEF cells were then infected with retrovirus (pMIY2-Cre-IRES-YFP) expressing Cre-YFP recombinase. Positive transfectants were obtained by fluorescence activated cell sorting to generate a $CCNC^{-/-}$ MEF pool. Single clones were further isolated by dilution plating with the deletion allele verified by PCR and Western blots.

Indirect Immunofluorescence

Cells were cultured on coverslips then fixed with 4% paraformaldehyde for 20 min, permeabilized with 0.2% Triton X-100 for 15 min, blocked with 2% BSA, and incubated with antibodies as indicated. The cells were mounted with DAPI-containing medium (Vector Labs) and the images were acquired with Nikon Eclipse 90i microscope equipped with a Retiga Exi CCD camera and NIS software for data analysis. DAPI (5 µg/ml) and Mitotracker Red (5 µg/ml) staining was used to identify nuclear and mitochondrial subcellular localization.

Survival and Stress Assays

Mammalian cells were seeded in 12-well plates at a density of $0.5\times10^5$ cells/well one day before stress treatment. $H_2O_2$ was added to cells immediately following a switch to serum-free medium. For cisplatin treatment, the drug was added to normal culture medium. Activation of the extrinsic pathway was accomplished with addition of TNF-☐ (5 ng/ml) and cycloheximide (10 µg/ml) for 24 h. Annexin V (BD Biosciences) assays were conducted as described by the manufacturer. MOMP studies were performed with exponential wild type or $CCNC^{-/-}$ MEF cultures were treated with $H_2O_2$ (0.4 mM) for three hours prior to staining with tetramethylrhodamine methyl ester (TMRM, Molecular Probes). TMRM staining was monitored by fluorescence activated cell analysis.

Mitochondrial Fragmentation Assays $CCNC^{+/+}$ and $CCNC^{-/-}$ MEF cells were treated with 0.4 mM $H_2O_2$ for 4 hrs. Mitochondrial morphology was monitored by MitoTracker Red staining. The cells were imaged with the 60× objective on the Nikon Eclipse C1Ti confocal microscope equipped with a Ds-Qi1MC CCD camera. The TAT-HAD peptide was added to log phase unstressed wild type MEF cultures for 3 h prior to image acquisition.

Yeast Growth and stress assays.

Cells were grown in either rich, non-selective medium (YPDA) or synthetic minimal medium (SC) allowing plasmid selection. Clonogenic viability studies were conducted with mid-log phase ($6\times10^6$ cells/ml) treated with 1 or 2 mM $H_2O_2$ for 2 h then serially diluted (1:10) and plated on the non-selective medium (YPDA). TUNEL positive cells were measured by fluorescence activated cell analysis using the Accuri C6 cell analyzer. All statistical analysis was performed using the student's T test with p<0.05 considered significant. All analyses were conducted with at least three independent cultures with 300 or more cells counted per timepoint.

Yeast Microscopy and Cell Analysis

Intracellular localization studies of chimeric fusion proteins were performed in fixed or living cells as indicated in the figure legends. Cells were fixed in 3.7% para-formaldehyde and stained with 4', 6-diamidino-2-phenylindole (DAPI). For all experiments, the cells were grown to mid-log ($5\times10^6$ cells/ml), treated with 1 mM $H_2O_2$ for time indicated in text then analyzed by fluorescence microscopy. Images were obtained using a Nikon microscope (model E800) with a 60× objective (Plan Fluor Oil, NA 1.3) and a CCD camera (RETIGA Exi). Data were collected using Autoquant® and processed using Image Pro software. All images were obtained using the same exposures for the course of the experiment. In all images, the bar indicates 5 µM.

EXAMPLE 3:

Cyclin C Stimulates Mitochondrial Fission and PCD Execution

The present inventors have characterized a conserved transcription factor, cyclin C, which mediates mitochondrial fission and PCD in both yeast and mammals. Under normal growth conditions, cyclin C and its kinase Cdk8 regulate transcription through association with the transcription machinery. However, a second role for cyclin C has been identified independent of Cdk8 or transcription. When yeast or mammalian cells are subjected to ROS or anti-cancer drugs, a portion of cyclin C exits the nucleus and associates with the mitochondria [Cooper, K. F., et al., Stress-Induced Nuclear-to-Cytoplasmic Translocation of Cyclin C Promotes Mitochondrial Fission in Yeast. Dev Cell, 2014. 28: p. 161-173; Adachi, Y. and H. Sesaki, Cyclin C: An Inducer of Mitochondrial Division Hidden in the Nucleus. Dev Cell, 2014. 28: p. 112-114]. At the mitochondria, cyclin C is required for stress-induced fission (FIG. 8A) through recruitment of Drp1, the GTPase that drives organelle scission. In addition, deleting CNCC protects MEFs from PCD that is reversed by reintroduction of the cyclin (FIG. 8B). This requirement for PCD is early in the pathway as cyclin C is required for MOMP (FIG. 8C). These results indicate that cyclin C is required for both mitochondrial fission and MOMP, two early events in the PCD pathway.

EXAMPLE 4:

Cyclin C Suppresses Hyperplasia in a Mouse Thyroid Cancer Model

Figure 9B:
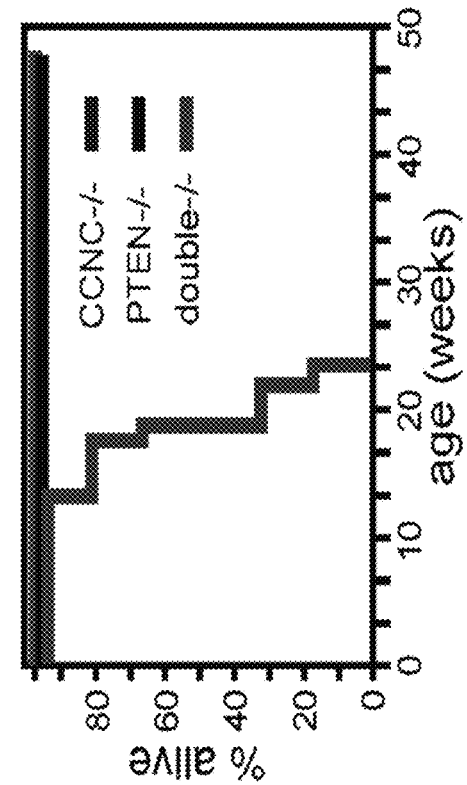
FIGS. 9A-9B demonstrate that cyclin C suppresses hyperplasia in a mouse thyroid cancer model.
Figure 9A:
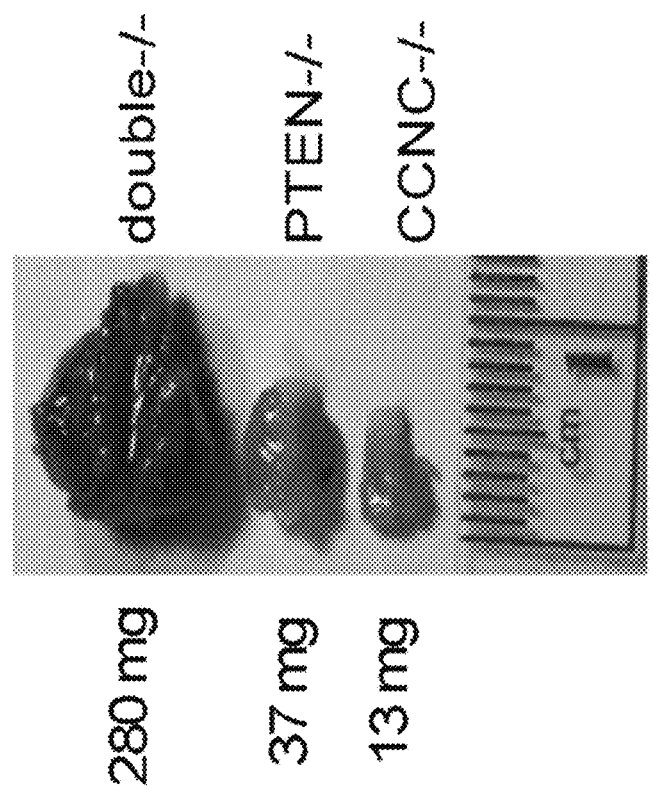
Figure 10A:
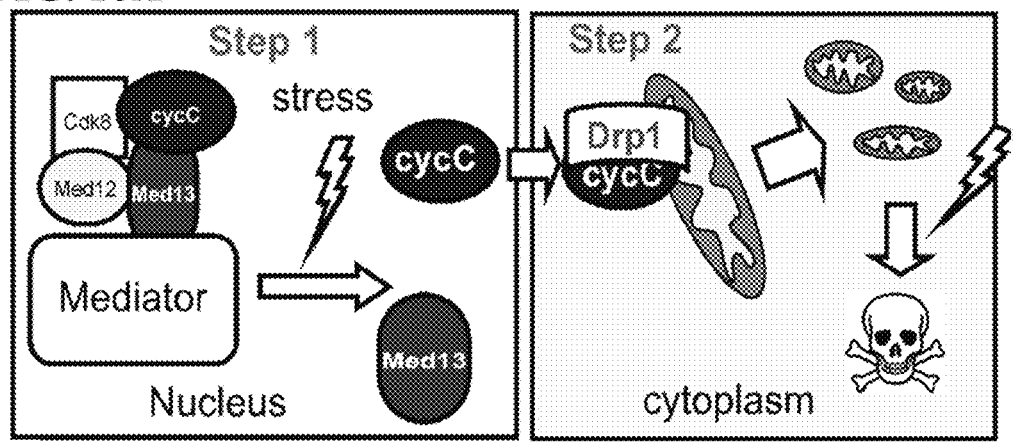
FIGS. 10A-10C show a two-step model for cyclin C-induced cell death.
Figure 10B:
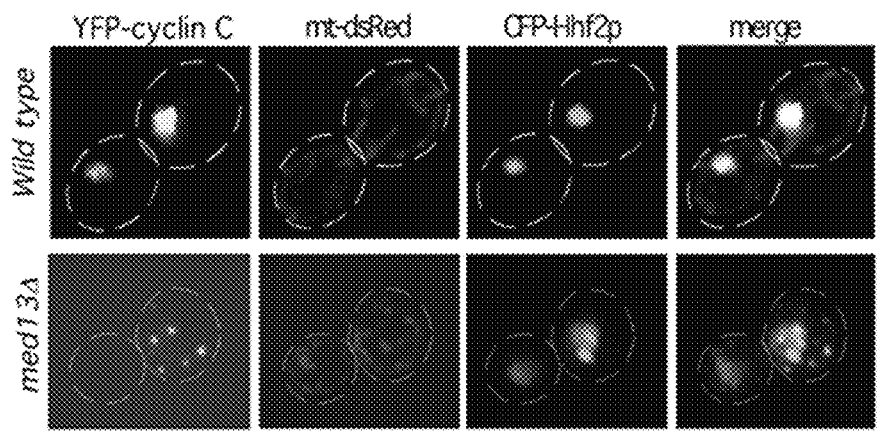
Figure 10C:
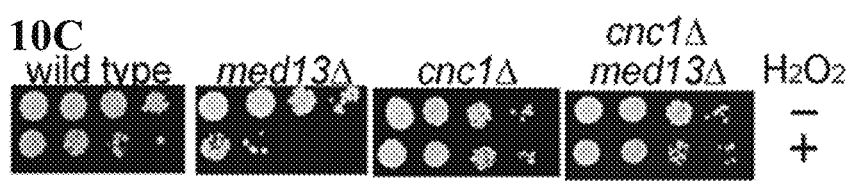

Consistent with a possible tumor suppressor role, the human cyclin C locus (6q21) has been shown to exhibit loss of heterozygosity (LOH) in 25% of primary osteosarcoma tumor cell lines examined. In addition, 6q21 was lost in 33% (n=12) of poorly differentiated thyroid tumors and 27% (n=15) of anaplastic malignancies. Interestingly, no loss of CCNC was observed in well differentiated, easily treated, thyroid disease. While not intending to be bound by any theory of operation, these results indicate that loss of cyclin C activity may be associated with tumor progression, but not initiation. To examine this possibility, cyclin C was deleted in a well-established $PTEN^{-/-}$ thyroid tumor mouse model [Antico Arciuch, V. G., et al., Thyrocyte-specific inactivation of p53 and Pten results in anaplastic thyroid carcinomas faithfully recapitulating human tumors. Oncotarget, 2011. 2(12): p. 1109-26.]. In $PTEN^{-/-}$ thyroids, the mice exhibited hyperplasia at birth but develop carcinomas and die approximately >1 yr [Di Cristofano, et al., Pten is essential for embryonic development and tumour suppression. Nat Genet, 1998. 19(4): p. 348-55]. However, by twenty weeks, $PTEN^{-/-}CCNC^{-/-}$ animals displayed a severely enlarged thymus (FIG. 9A) resulting in premature death (FIG. 9B). Pathology of these tissues revealed extensive hyperplasia with fibrotic and early cancer lesions (data not shown).

EXAMPLE 5:

Rational drug designs have been used to produce agents that can interfere with protein:protein interactions [Plescia, J., et al., Rational design of shepherdin, a novel anticancer agent. Cancer Cell, 2005. 7(5): p. 457-68]. These inhibitors can be small molecules derived from the structural analysis of protein binding domains [Sillerud, L. O. and R. S. Larson, Design and structure of peptide and peptidomimetic antagonists of protein-protein interaction. Curr Protein Pept Sci, 2005. 6(2): p. 151-69] or small peptides that mimic these motifs [Zhou, P., C. et al., Computational peptidology: a new and promising approach to therapeutic peptide design. Curr Med Chem, 2013. 20(15): p. 1985-96].

A highly conserved region of cyclin C has been identified [Cooper, K. F. and R. Strich, Functional analysis of the Ume3p/Srb11p-RNA polymerase II holoenzyme interaction. Gene Expr, 1999. 8(1): p. 43-57; Cooper, K. F., S. Khakhina, S. K. Kim, and R. Strich, Stress-Induced Nuclear-to-Cytoplasmic Translocation of Cyclin C Promotes Mitochondrial Fission in Yeast, Dev Cell, 2014. 28: p. 161-173.], boxed, FIG. 11A) that is responsible for Med13 binding in yeast. To test the feasibility of targeting this region to disrupt Med13-cyclin C interaction, a 19 residue peptide (line above amino acid sequences in FIG. 11A) (residues 14-32 of SEQ ID NO:9) was fused to the HIV TAT basic region that promotes membrane translocation [Heitz, F., M. C. Morris, and G. Divita, Twenty years of cell-penetrating peptides: from molecular mechanisms to therapeutics. Br J Pharmacol, 2009, 157(2): p. 195-206]. As a control, a peptide was synthesized containing the TAT domain fused to a scrambled cyclin C sequence.

Incubation of MEF cells with each of these peptides provided very different results. The control peptide-treated cells displayed normal nuclear cyclin C localization and elongated mitochondria (FIG. 11B, top panels). However, cells treated with the TAT-HAD peptide exhibited nuclear to cytoplasmic cyclin C translocation (FIG. 11B, lower panels). In addition, cyclin C associated with the mitochondria that exhibited an abnormal fragmented morphology (arrows). These results indicate that targeting the cyclin C-Med13 interaction with a peptide can disassociate this complex leading to cytoplasmic cyclin C and mitochondrial fragmentation. However, this phenotype was transient and was lost within 24 hours.

EXAMPLE 6:

Targeting the Med13 Interaction Domain with "Stapled" Peptides

To address potential issues observed with the cyclin C peptides described above, all hydrocarbon "stapled" peptides directed to cyclin C are made. Stapled peptides are synthesized with the introduction of two α-methyl, α-alkenylglycine residues spaced to be on the same side of an alpha helix (e.g., i and i+4 or i and i+7). While not intending to be bound by any theory of operation, stapled peptides may be used to stably disrupt cyclin C-Med13 interaction inside cells.

EXAMPLE 7:

Assay of S-HAD Activity

To measure the impact of S-HAD peptide addition a dose-dependent change in cyclin C localization is monitored; along with mitochondrial morphology and drug sensitivity. The toxicity of the peptide alone in transformed versus untransformed cell lines is examined. Low-dose cancer chemotherapeutic regimens is administered in combination with the peptide to determine if the threshold of working drug concentrations is reduced. The peptides are added individually and together. The cell lines used are non-transformed controls (MEF, WI-38 fibroblasts) and tumor cell lines that do (Hela) or do not (MCF-7) demonstrate normal cyclin C regulation of drug sensitivity (see below). Additional cell lines that display cyclin C-dependent drug regulation may be used.

Figure 15B:
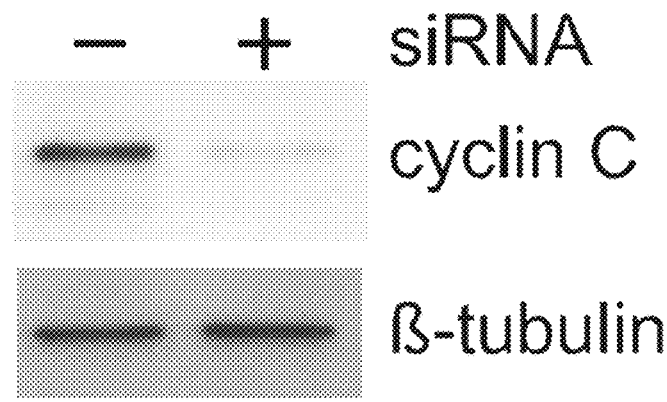
Figure 15C:
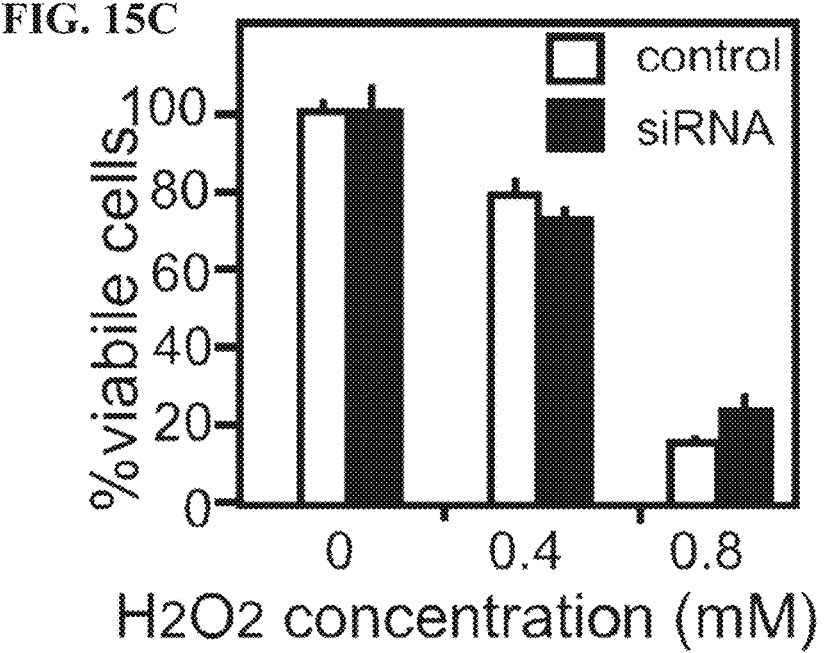

EXAMPLE 8:

Two cell lines were identified, Hela and MCF-7, which exhibited normal and abnormal cyclin C relocalization, respectively. In response to $H_2O_2$, cyclin C translocated from the nucleus to the cytoplasm in HeLa cells (FIG. 14A). Increased magnification revealed that cyclin C associated with the mitochondria (FIG. 14B). To evaluate the role of cyclin C in PCD execution, CCNC specific siRNAs were used to knockdown cyclin C. The knockdown efficiency was about 70% compared to control (FIG. 14C). Cyclin C knockdown HeLa cells were resistant to ROS (FIG. 14D). Conversely, cyclin C remained nuclear following $H_2O_2$ or cisplatin treatment in MCF-7 breast cancer cell line (FIG. 15A, top panels). However, this is not a property of all breast cell lines as the immortalized, non-tumorigenic MCF-10A cells displayed normal cyclin C relocalization and mitochondrial fission (bottom panels). In MCF-7 cells, knocking down cyclin C (FIG. 15B) did not impact cell viability in response to $H_2O_2$ treatment (FIG. 15C).

EXAMPLE 9:

Defining the Spectrum of Drug-Cell Type Combinations Regulated by Cyclin C

A collection containing multiple validated cell lines representing major tumor types including lung, mammary, melanoma, ovarian, prostate and kidney is used (for example, the NCI-60 cell line collection). Cell lines established from primary and metastatic lesions as well as samples taken before and following treatment may also be used (and may be found in, e.g., the NCI-60 cell line collection). The individual cell lines are treated with CCNC specific siRNAs or a mock control then assayed as described below. Cyclin C knockdown efficiency is confirmed by Western blot analysis. If cyclin C knockdown is resistant to these conditions, an shRNA approach to reduce cyclin C may be used.

Drug treatments. While not intending to be bound by any theory of operation, that cyclin C may be required for normal PCD execution in response to cisplatin (FIGS. 8A-8D) as well as more general oxidative damage (FIGS. 14A-14D). Therefore, the drugs are chosen to provide a comprehensive sampling of compounds currently being used clinically with many exerting their effects through ROS production [Lau, A. T., Y. Wang, and J. F. Chiu, Reactive oxygen species: current knowledge and applications in cancer research and therapeutic, J Cell Biochem, 2008. 104(2): p. 657-67]. For example, Paclitaxel, the anti-microtubule drug also reduces GSH levels; DNA damaging agents bleomycin and cisplatin; Doxorubicin, a topoisomerase II inhibitor that generates ROS through aberrant quinone redox cycling and Tamoxifen, an antiestrogen that targets mitochondrial integrity. In addition, drugs not known to induce ROS (vincristine, etoposide), are examined. Drug treatment regimens are modeled after similar studies known to the art. Cell lines are identified in which cyclin C knockdown results in protection from a drug treatment.

Hypoxia. The cell lines are subjected to hypoxic (1-2% $O_2$) or anoxic (<0.5% $O_2$) conditions for 24, 48 and 72 hrs. Cell viability, cyclin C relocalization and mitochondrial morphology is assayed as described below. Hypoxia represents an early stress solid tumors encounter.

Viability studies. The cells are seeded in 12-well plates at a density of $0.5 \times 10^5$ cells/well one day before drug treatment. Annexin V and propidium iodide (PI) staining assays are quantified by fluorescence activated cell analysis to measure PCD and necrosis, respectively. Assays are performed with three biological replicates with statistical analysis using the student's T test (p<0.05 considered significant).

Cyclin C mitochondrial re-localization and mitochondrial fission. Cyclin C relocalization and mitochondrial fission is monitored by indirect immunofluorescence and mitochondrial specific stains using standard protocols. Cell lines that do not exhibit cyclin C relocalization, and display PCD insensitive to knockdown experiments (similar to MCF-7), are assayed to determine if these cell lines can be "rescued" by allowing cyclin C relocalization following S-HAD peptide addition.

EXAMPLE 10:

Cyclin C is Sufficient to Induce Mitochondrial Fragmentation

To examine whether cyclin C was sufficient to induce fission or if additional stress-specific signals were required, permeabilized $CCNC^{-/-}$MEF cells were used and *E. coli* purified human GST-cyclin C (Hs GST-cyclin C). The $CCNC^{-/-}$null cell line was employed to avoid any contribution from endogenous cyclin C. GST-cyclin C or GST (~4 nM) was added to digitonin treated cells and mitochondrial morphology was monitored in living cells by confocal microscopy. Images were collected for 18 min at 2 min increments. Prior to addition of the fusion proteins, the percentage of cells exhibiting predominantly fragmented mitochondria was calculated for each dish. Cells were considered having fragmented mitochondria if they did not possess ≥10 mitochondrion with a length greater than 10 μm. 8-10% of the cells exhibited a fragmented morphology prior to treatment. Deconvolved images reveled little detectable changes in mitochondrial morphology in the GST treated cultures up to 18 min (9.3%). However, significant fragmentation of the mitochondria was observed when the human GST-cyclin C was added to cells beginning by 10 min with 94% of the culture exhibiting complete fragmentation by 18 min. These results indicate that cyclin C is sufficient to induce mitochondrial fission without an added stress signal. To determine if this function is conserved, the activity of the yeast cyclin C fused to GST (GST-cyclin C Sc) was also examined. The yeast fusion protein was as efficient inducing mitochondrial fission as the human cyclin C indicating that this activity is conserved. To determine if the quantity of GST-cyclin C added was rate limiting, this experiment was repeated with twice the GST-cyclin C Hs concentration as before. These studies revealed a more rapid response with total mitochondrial fragmentation occurring by 8 min. These results indicate that the relocalization rate of cyclin C may help the cell regulate the kinetics of mitochondrial fission.

Previous studies found that Drp1 function is controlled by several post-translational modifications such as phosphorylation, SUMOylation; and ubiquitylation (Horn et al., 2011). For phosphorylation, both inhibitory and stimulatory modifications have been identified. For example, cyclin B-Cdk1 phosphorylation at the G2/M boundary stimulates Drp1 activity to induce fission to promote mitochondrial partitioning during mitosis. This modification is clearly observed in cells arrested at the G2/M boundary following addition of the microtubule destabilizing agent nocodazole. Therefore, one possibility is that cytoplasmic cyclin C is now free to interact with another Cdk to modify Drp1 and induce fission. However, no increase was found in Drp1 phosphorylation at the activating serine (Ser616) in Hela cells subjected to $H_2O_2$ or in permeabilized $CCNC^{-/-}MEF$ cells treated with GST-cyclin C. These results indicate that enhanced Ser616 phosphorylation is not required for elevated Drp1 activity in stressed cells. Quantitation of the Ser616 phosphorylation signal indicated that this modification was reduced in permeabilized cells treated with GST-cyclin C. It is possible that the accelerated fission in these experiments results in de-phosphorylation of Ser616 helping attenuate mitochondrial fragmentation.

All references cited herein are incorporated by reference herein in their entireties.

We claim:

1. A method of inhibiting growth of a tumor cell or sensitizing a tumor cell to an anti-cancer agent, the method comprising contacting the tumor cell with a peptide consisting of amino acid sequence of SEQ ID NO:8 or a peptide consisting of amino acid sequence of SEQ ID NO:8 which is conjugated with an additional peptide capable of promoting cellular membrane translocation.

2. The method of claim 1, wherein the additional peptide has an amino acid sequence selected from the group consisting of HIV TAT translocation sequence (SEQ ID NO:1); Penetratin (SEQ ID NO:2); and FHV (SEQ ID NO:3).

3. The method of claim 1, wherein the peptide is part of a pharmaceutical composition.

4. The method of claim 3, wherein the pharmaceutical composition further comprises at least one further therapeutic agent.

5. The method of claim 4, wherein the further therapeutic agent is selected from the group consisting of cisplatin, paclitaxel, etoposide, aminolevulinic acid, bleomycin, doxorubicin, and tamoxifen.

6. A method of treating cancer in a subject, the method comprising administering to the subject in need thereof a therapeutically effective amount of a peptide consisting of amino acid sequence of SEQ ID NO:8 or a peptide consisting of amino acid sequence of SEQ ID NO:8 which is conjugated with an additional sequence capable of promoting cellular membrane translocation.

7. The method of claim 6, wherein the additional peptide comprises an amino acid sequence selected from the group consisting of HIV TAT translocation sequence (SEQ ID NO:1); Penetratin (SEQ ID NO:2); and FHV (SEQ ID NO:3).

8. The method of claim 7, wherein the subject is further administered an anti-cancer agent selected from the group consisting of cisplatin, paclitaxel, etoposide, aminolevulinic acid, bleomycin, doxorubicin, and tamoxifen.

9. The method of claim 6, wherein the cancer is selected from the group consisting of lung, mammary, melanoma, ovarian, prostate, thyroid, pancreatic, mesothelioma, testicular, lymphoma, leukemia, and kidney.

10. The method of claim 6, wherein the peptide is alpha-helical and cross-linked by a linker that cross-links a first amino acid to a second amino acid in the peptide.

11. The method of claim 10, wherein the linker comprises two a-methyl, α-alkenyl glycine residues.

12. The method of claim 1, wherein the tumor cell is selected from the group consisting of lung, mammary, melanoma, ovarian, prostate, thyroid, pancreatic, mesothelioma, testicular, lymphoma, leukemia, and kidney tumor cell.

13. The method of claim 1, wherein the peptide is alpha-helical and cross-linked by a linker that cross-links a first amino acid to a second amino acid in the peptide.

14. The method of claim 13, wherein the cross-linked peptide has enhanced cell penetrability relative to the corresponding non-cross-linked peptide.

15. The method of claim 14, wherein the cross-linked peptide has a more stable alpha-helix structure relative to the corresponding non-cross-linked peptide.

16. The method of claim 13, wherein the linker comprises two α-methyl, α-alkenyl glycine residues.

* * * * *